(12) United States Patent
Goble et al.

(10) Patent No.: US 7,344,532 B2
(45) Date of Patent: Mar. 18, 2008

(54) ELECTROSURGICAL GENERATOR AND SYSTEM

(75) Inventors: Nigel Mark Goble, Cardiff (GB); Francis Amoah, Cardiff (GB); Colin C. O. Goble, South Oxfordshire (GB)

(73) Assignee: Gyrus Medical Limited, Cardiff (GB)

( * ) Notice: Subject to any disclaimer, the term of this patent is extended or adjusted under 35 U.S.C. 154(b) by 412 days.

(21) Appl. No.: 11/006,552

(22) Filed: Dec. 8, 2004

(65) Prior Publication Data

US 2005/0113820 A1 May 26, 2005

Related U.S. Application Data

(63) Continuation-in-part of application No. 10/858,406, filed on Jun. 2, 2004, now Pat. No. 7,282,048, which is a continuation-in-part of application No. 10/378,676, filed on Mar. 5, 2003, now Pat. No. 6,966,907, which is a continuation-in-part of application No. 10/228,284, filed on Aug. 27, 2002, now Pat. No. 6,984,231.

(60) Provisional application No. 60/314,650, filed on Aug. 27, 2001.

(30) Foreign Application Priority Data

May 27, 2002 (GB) .................. 0212162.2
Nov. 12, 2004 (GB) .................. 0425051.0

(51) Int. Cl.
*A61B 18/18* (2006.01)
(52) U.S. Cl. .................. 606/34; 606/37; 606/38; 606/39; 606/40; 606/41; 606/48; 606/50; 606/51
(58) Field of Classification Search .................. 606/37, 606/38
See application file for complete search history.

(56) References Cited

U.S. PATENT DOCUMENTS 4,116,198 A 9/1978 Roos (Continued)

FOREIGN PATENT DOCUMENTS

DE 199 43 792 A1 4/2001

(Continued)

OTHER PUBLICATIONS

Search Report for corresponding foreign Application No. GB0425051.0, dated Jan. 25, 2005.

(Continued)

*Primary Examiner*—Lee S. Cohen
(74) *Attorney, Agent, or Firm*—Nixon & Vanderhye P.C.

(57) ABSTRACT

In an electrosurgical generator for generating radio frequency power, the generator comprises a radio frequency output stage having three or more output connections, one or more sources of output power coupled to the output stage, and a controller operable to cause the generator to supply a first cutting RF waveform to the output connections or a second coagulating RF waveform to the output connections. In a combined mode, the controller causes the generator to deliver both first and second RF waveforms, the controller including means for feeding the waveforms to the output connections such that the first RF waveform is delivered between a first pair of the output connections, and the second RF waveform is delivered between a second pair of the output connections. The combined mode is adjustable between various settings, each setting having a different proportion of the first and second RF waveforms. In response to a operator-actuated input signal, the controller causes the generator to supply an output waveform starting at a predetermined start setting, ending at a predetermined end setting, and changing between the start and end settings according to a predetermined progression.

19 Claims, 17 Drawing Sheets

U.S. PATENT DOCUMENTS

| | | | |
|---|---|---|---|
| 4,739,759 A | 4/1988 | Rexroth et al. |
| 5,160,334 A | 11/1992 | Billings et al. |
| 5,976,132 A | 11/1999 | Morris |
| 6,113,596 A | 9/2000 | Hooven et al. |
| 6,174,309 B1 | 1/2001 | Wrublewski et al. |
| 6,416,509 B1 | 7/2002 | Goble et al. |
| 6,679,882 B1 | 1/2004 | Kornerup |
| 2002/0165531 A1 | 11/2002 | Goble |
| 2003/0073990 A1 | 4/2003 | Goble et al. |
| 2003/0163123 A1 | 8/2003 | Goble et al. |
| 2003/0163124 A1 | 8/2003 | Goble |
| 2004/0006340 A1 | 1/2004 | Latterell et al. |
| 2004/0097913 A1 | 5/2004 | Refior et al. |

FOREIGN PATENT DOCUMENTS

| | | |
|---|---|---|
| EP | 0 754 437 A2 | 1/1997 |
| EP | 1 287 788 A1 | 3/2003 |
| EP | 1287788 A1 | 5/2003 |
| WO | WO 96/37156 | 11/1996 |
| WO | WO96/37156 A1 | 11/1996 |
| WO | WO 98/38932 A1 | 9/1998 |
| WO | WO 00/53112 | 9/2000 |
| WO | WO2004/078050 A3 | 9/2004 |

OTHER PUBLICATIONS

International Search Report in International Application No. PCT/GB2004/000917, Oct. 6, 2004.

Official Partial International Search Report in International Application No. PCT/GB2004/000917 (3 pages).

Search Report in UK Application No. GB 0305018.4, Jun. 19, 2003.

International Search Report in corresponding International Application No. PCT/GB2005/003721, mailed Feb. 12, 2005.

Written Opinion in corresponding International Application No. PCT/GB2005/003721, mailed Feb. 12, 2005.

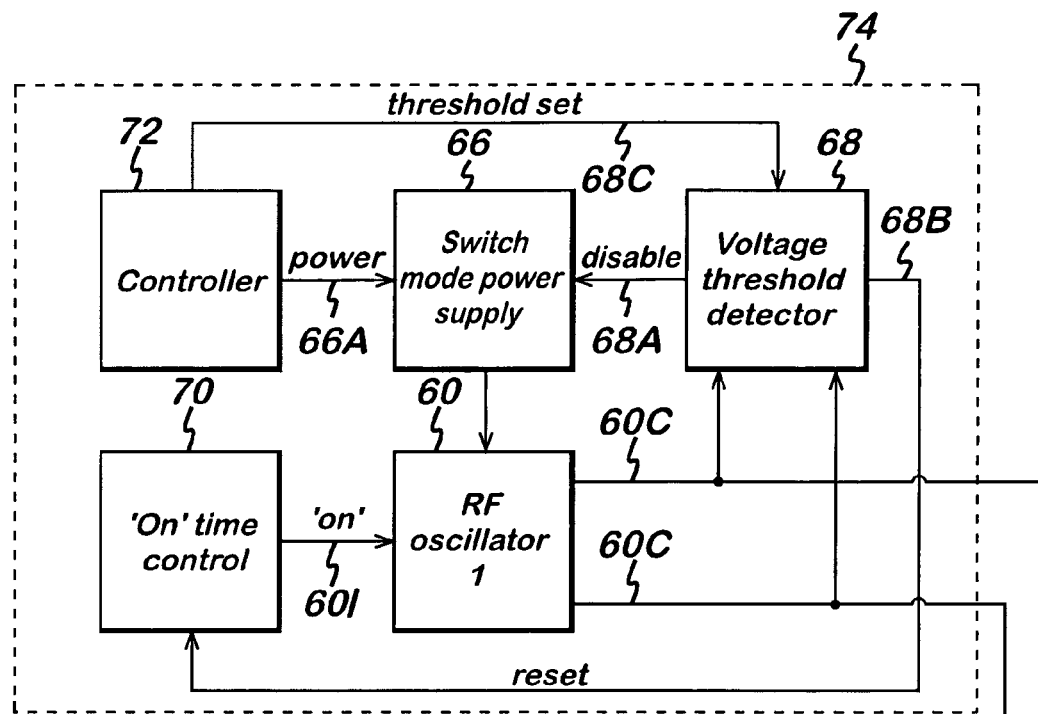
Fig. 9
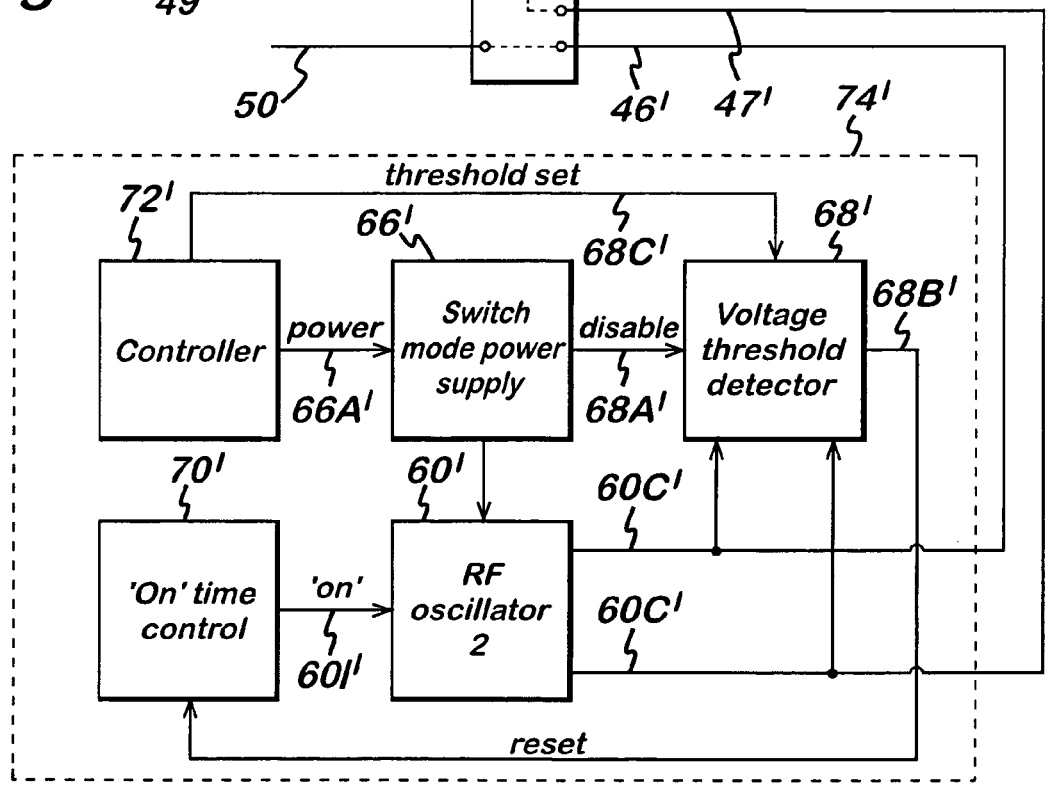

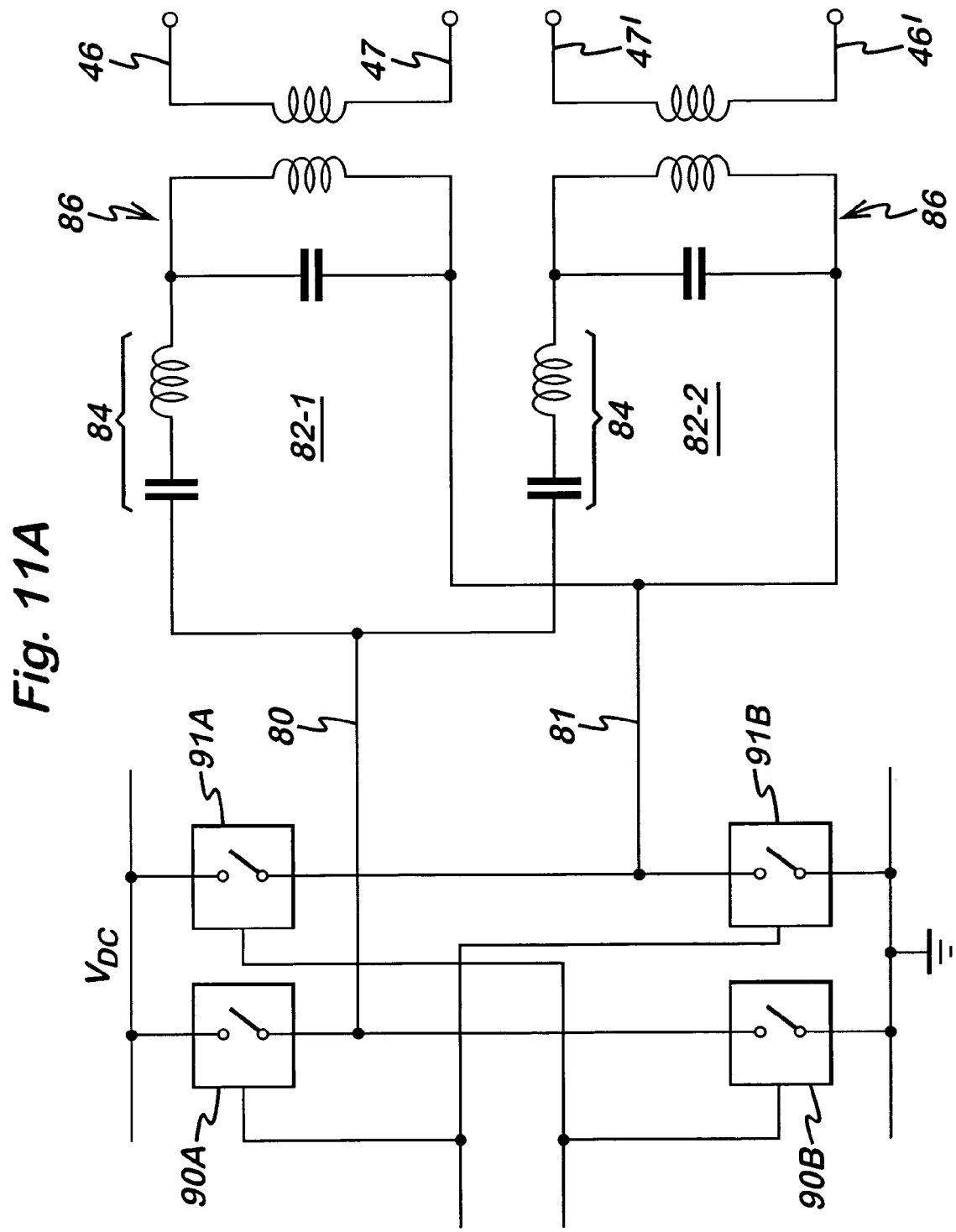

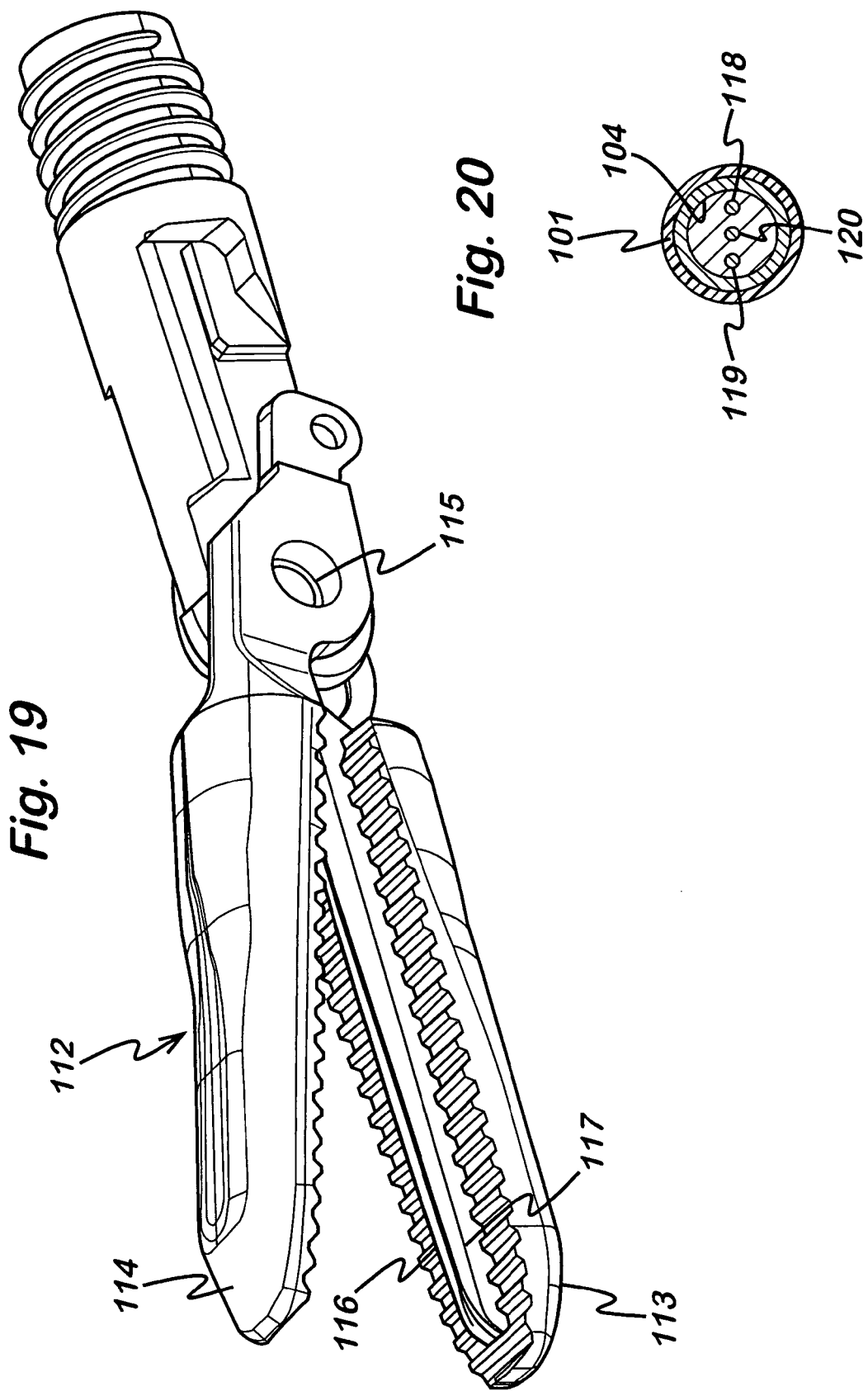

ELECTROSURGICAL GENERATOR AND SYSTEM

CROSS-REFERENCE TO RELATED APPLICATIONS

This application is a continuation-in-part of U.S. patent application Ser. No. 10/858,406, filed Jun. 2, 2004, now U.S. Pat. No. 7,282,048, which is a continuation-in-part of U.S. patent application Ser. No. 10/378,676, filed Mar. 5, 2003, now U.S. Pat. No. 6,966,907, which is a continuation-in-part of U.S. application Ser. No. 10/228,284, filed Aug. 27, 2002, now U.S. Pat. No. 6,984,231, which claims the benefit of U.S. Provisional Patent Application Ser. No. 60/314,650, filed Aug. 27, 2001, the entire contents of all of which are incorporated by reference in this application.

FIELD OF THE INVENTION

This invention relates to an electrosurgical generator, and to an electrosurgical system comprising a generator and an electrosurgical instrument with two or more treatment electrodes. Such systems are commonly used for the cutting and/or coagulation of tissue in surgical intervention, most commonly in "keyhole" or minimally invasive surgery, but also in laparoscopic or "open" surgery.

BACKGROUND OF THE INVENTION

It is known to provide electrosurgical generators which provide different radio frequency signals for cutting and coagulation, and also to provide a blended signal in which the generator rapidly alternates between the signals for cutting and coagulation. Our U.S. Pat. No. 6,416,509 and also U.S. Pat. No. 3,885,569 to Judson describe blended signals of this type.

SUMMARY OF THE INVENTION

According to the present invention there an electrosurgical generator system is provided for generating radio frequency power, the generator comprising:
(i) a radio frequency output stage having three or more output connections,
(ii) one or more radio frequency sources coupled to the output stage,
(iii) a controller operable to cause the system to supply a first cutting RF waveform to the output connections or a second coagulating RF waveform to the output connections, and, in a combined mode, to deliver both first and second RF waveforms, the controller including means for feeding the waveforms to the output connections such that the first RF waveform is delivered between a first pair of the output connections, and the second RF waveform is delivered between a second pair of the output connections, the arrangement of the system being such that the combined mode is adjustable between various settings, each setting having a different proportion of the first and second RF waveforms, and that, in response to a operator-actuated input signal, the controller causes the system to supply an output waveform sequence starting at a predetermined start setting, ending at a predetermined end setting, and changing between the start and end settings according to a predetermined progression.

Our pending European patent application EP 1287788 describes an electrosurgical system in which the operator can select between a cutting signal and a coagulation signal. When the cutting signal is selected, it is supplied to one pair of electrosurgical electrodes, and when the coagulation signal is selected it is supplied to a different pair of electrosurgical electrodes. Our pending US application 2003-0163124 is an improvement to this system, in that it also provides a combined mode of operation, but with the different components of the combined signal being supplied to different sets of electrosurgical electrodes. The present invention provides a further improvement in which the output waveform sequence progresses from a predetermined start setting to a predetermined end setting.

The progression of the waveform sequence offers several advantages to the user. When an electrosurgical instrument is being used to cut tissue, particularly thick tissue, it is difficult to coagulate the tissue completely before cutting commences. If prolonged coagulation is performed before cutting commences, there is the risk that some parts of the tissue will become desiccated. Desiccated tissue is unreceptive to RF energy, and hence a subsequently applied cutting waveform will not be effective. Conversely, if coagulation is incomplete, there is the risk that bleeding will be encountered during cutting. Thus surgeons tend to switch repeatedly between the coagulation and cutting modes of electrosurgical generators as bleeding is encountered (necessitating the repeated operation of the footswitch or the like). The generator described in the present application maintains an element of coagulation throughout the cutting process, with a different proportion of the cutting and coagulation waveforms as the tissue treatment progresses.

Preferably, the first RF cutting waveform is a waveform in which the radio frequency output voltage developed across the output connections is limited to at least a first predetermined threshold value for cutting or vaporisation of tissue, and the second RF coagulation waveform is a waveform in which the radio frequency output voltage developed across the output connections is limited to a second threshold value for coagulation.

The "combined mode" of the generator can be provided in different ways. In one arrangement, the generator system comprises a single source of radio frequency power, and, in the combined mode, the controller is operable to cause the generator system to alternate constantly between delivering the first cutting RF waveform and the second coagulating RF waveform. This is the more traditional "blended" signal of U.S. Pat. Nos. 6,416,509 and 3,885,569. Alternatively, the generator system comprises at least first and second sources of radio frequency power, operating at different frequencies, the first source of radio frequency power being adapted to deliver the first cutting RF waveform, and the second source of radio frequency power being adapted to deliver the second coagulating RF waveform, and, in the combined mode, the controller is operable to cause the generator system to deliver both the first and second RF waveforms simultaneously. This is a different arrangement in which the output of two RF sources is supplied to the instrument simultaneously. Both arrangements have the effect, however, of supplying both cutting and coagulating RF signals to the electrosurgical instrument while the instrument is in use.

In a preferred arrangement, the various settings each have a first predetermined duty cycle of the first RF waveform, and a second predetermined duty cycle of the second RF waveform. Preferably, the predetermined start setting has a waveform combination such that the proportion of the second RF waveform is greater than the proportion of the first RF waveform. Additionally, the predetermined end setting has a waveform combination such that the proportion of the first RF waveform is greater than the proportion of the second RF waveform. The start setting conveniently is a waveform having a second duty cycle that is between 70% and 100% of the overall waveform, typically between 90% and 100% of the overall delivered output. Alternatively or additionally, the end setting is a waveform having a first duty cycle that is between 70% and 100% of the overall waveform, typically between 90% and 100% of the overall delivered output. In a typical arrangement, the start setting is a combined waveform having a first duty cycle that is 100% of the overall delivered output, and the end setting is a blended waveform having a second duty cycle that is 90% of the overall delivered output.

In the above-described arrangement, not only does the generator maintain an element of coagulation throughout the cutting process, but the proportion of the coagulation waveform is greater towards the start of the process. Thus, if the surgeon encounters bleeding during the electrosurgical cut, the surgeon releases and then re-activates the footswitch or other actuating mechanism. This re-sets the progression to the start setting, with a proportionately high degree of coagulation therein.

Preferably, the predetermined progression from the start setting to the end setting is an even progression over a predetermined time. This ensures that the electrosurgical cutting of the tissue will occur as soon as it is feasible to do so. Alternatively, the progression may not be an even progression, but for example may have an initial period at a constant setting (e.g. a predominantly coagulative waveform), followed by a progression after this initial period to the end setting (e.g. a predominantly cutting waveform). Regardless of whether the progression is an even one, the time taken for the generator to progress from its start setting to its end setting may be varied, depending on the type of instrument connected to the generator, or the type of tissue being treated.

The controller is preferably adapted to supply an overall output waveform sequence in the form of a series of pulses, conveniently at a frequency of between 0.5 and 50 Hz, and typically at a frequency of between 15 and 25 Hz.

The invention further resides in an electrosurgical system including an electrosurgical generator apparatus for generating radio frequency power, and an electrosurgical instrument including at least three electrodes, the generator apparatus comprising (i) a radio frequency output stage having at least two output connections in electrical communication with the electrodes of the instrument, (ii) a power supply coupled to the output stage for supplying power to the output stage, (iii) a controller operable to cause the generator apparatus to supply a blended output waveform alternating constantly between a first output waveform across the output connections in which the radio frequency output voltage developed across the output connections is limited to at least a first predetermined threshold value for cutting or vaporisation of tissue, and a second output waveform across the output connections in which the radio frequency output voltage developed across the output connections is limited to a second threshold value for coagulation, the controller including means for feeding the waveforms to the output connections such that the first output waveform is delivered between a first pair of the output connections, and the second output waveform is delivered between a second pair of the output connections, the controller being capable of causing the generator apparatus to deliver the waveform in various settings, the various settings each having a first predetermined duty cycle of the waveform that is limited to the first threshold value for cutting or vaporisation, and a second predetermined duty cycle of the waveform that is limited to the second threshold value for coagulation, the arrangement of the system being such that, in response to a operator-actuated input signal, the controller causes the generator apparatus to supply an output waveform sequence starting at a predetermined start setting, ending at a predetermined end setting, and changing between the start and end settings according to a predetermined progression. Preferably, at least two of the electrodes are in the form of a pair of jaws.

Accordingly, the invention extends to an electrosurgical system comprising (i) a bipolar electrosurgical instrument including a handle, a jaw assembly arranged such that manipulation of the handle allows the opposed jaws of the jaw assembly to be opened and closed with respect to one another; a first of said opposed jaws having at least a first coagulating electrode; the other of said opposed jaws having at least a second coagulating electrode; and a cutting electrode and separated from the second coagulating electrode by an insulating member, and (ii) electrosurgical generator apparatus comprising one or more sources of RF output power, a controller operable to control the generator apparatus such that it is capable of providing a first cutting RF waveform to the electrosurgical instrument or a second coagulating RF waveform to the electrosurgical instrument, and, in a combined mode, to deliver both first and second RF waveforms, the waveforms being fed to the electrosurgical instrument such that, in the combined mode, the cutting RF waveform is delivered between the cutting electrode and at least one of the first and second coagulating electrodes, and the coagulating RF waveform is delivered between the first and second coagulating electrodes, the combined mode being adjustable between various settings, each setting having a different proportion of the first and second RF waveforms, the arrangement of the generator apparatus being such that, in response to a operator-actuated input signal, the controller causes the generator apparatus to supply an output waveform sequence starting at a predetermined start setting, ending at a predetermined end setting, and changing between the start and end settings according to a predetermined progression.

Finally, the invention resides in a method of electrosurgically modifying tissue comprising the steps of (i) contacting the tissue with an electrosurgical instrument including at least first and second electrodes, (ii) supplying to the first and second electrodes an electrosurgical waveform combination including a first proportion comprising an RF cutting waveform and a second proportion comprising an RF coagulating waveform, and (iii) varying the first and second waveform proportions according to a predetermined progression.

The invention will be further described below, by way of example only, with reference to the accompanying drawings.

BRIEF DESCRIPTION OF THE DRAWINGS

In the drawings:

FIG. 9 is a block diagram of an alternative embodiment of generator system in accordance with the present invention, FIGS. 11A and 11B are yet further alternative systems for feeding cut and coagulation outputs automatically to different respective electrode pairs, FIG. 19 is a perspective view of the jaw assembly of the instrument of FIG. 18, FIG. 20 is a cross-sectional view of the body of the instrument of FIG. 18.

DETAILED DESCRIPTION OF THE PREFERRED EMBODIMENTS OF THE INVENTION

Figure 1:
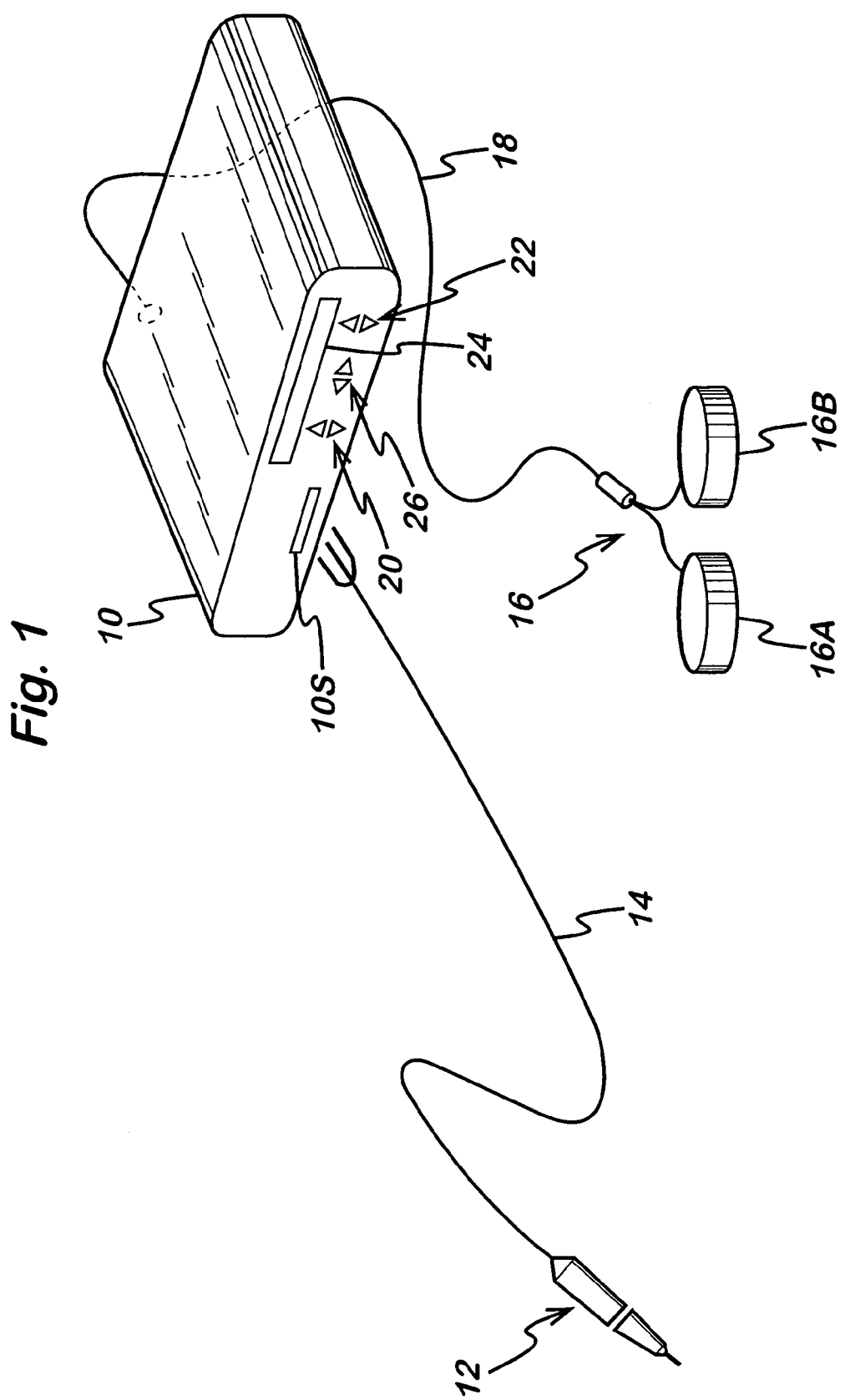
FIG. 1 is a schematic diagram of an electrosurgical system in accordance with the present invention.

Referring to FIG. 1, a generator 10 has an output socket 10S providing a radio frequency (RF) output for an instrument 12 via a connection cord 14. Activation of the generator may be performed from the instrument 12 via a connection in cord 14 or by means of a footswitch unit 16, as shown, connected to the rear of the generator by a footswitch connection cord 18. In the illustrated embodiment footswitch unit 16 has two pedals 16A and 16B for selecting a coagulation mode and a cutting mode of the generator respectively. The generator front panel has push buttons 20 and 22 for respectively setting coagulation and cutting power levels, which are indicated in a display 24. Push buttons 26 are provided as an alternative means for selection between coagulation and cutting modes.

Figure 2:
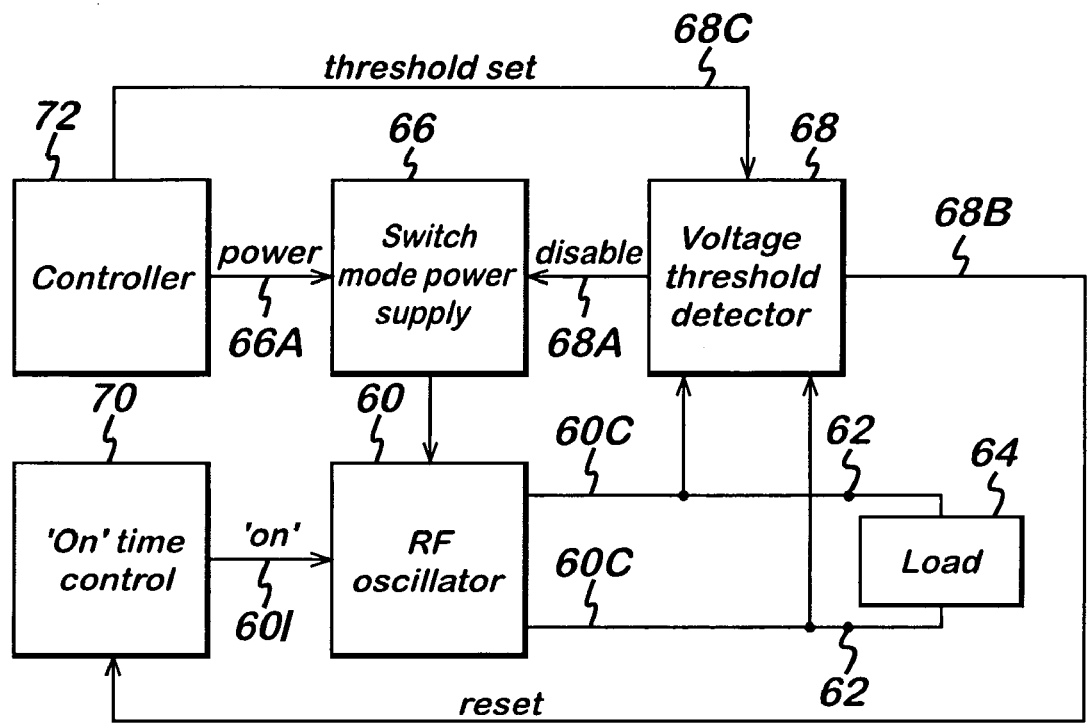
FIG. 2 is a block diagram of the generator of FIG. 1.

Referring to FIG. 2, the generator comprises a radio frequency (RF) power oscillator 60 having a pair of output lines 60C for coupling to the instrument 12. The instrument 12 is shown in FIG. 2 in the form of an electrical load 64. Power is supplied to the oscillator 60 by a switched mode power supply 66. In the preferred embodiment, the RF oscillator 60 operates at about 400 kHz, with any frequency from 300 kHz upwards into the HF range being feasible. The switched mode power supply typically operates at a frequency in the range of from 25 to 50 kHz. Coupled across the output lines 60C is a voltage threshold detector 68 having a first output 68A coupled to the switched mode power supply 16 and a second output 68B coupled to an "on" time control circuit 70. A microprocessor controller 72 coupled to the operator controls and display (shown in FIG. 1) is connected to a control input 66A of the power supply 66 for adjusting the generator output power by supply voltage variation and to a threshold-set input 68C of the voltage threshold detector 68 for setting peak RF output voltage limits.

In operation, the microprocessor controller 72 causes power to be applied to the switched mode power supply 66 when electrosurgical power is demanded by the surgeon operating an activation switch arrangement which may be provided on a hand-piece or footswitch (see FIG. 1). A constant output voltage threshold is set independently on the supply voltage via input 68C according to control settings on the front panel of the generator (see FIG. 1). Typically, for desiccation or coagulation the threshold is set at a desiccation threshold value between 150 volts and 200 volts. When a cutting or vaporisation output is required the threshold is set to a value in the range of from 250 or 300 volts to 600 volts. These voltage values are peak values. Their being peak values means that for desiccation at least it is preferable to have an output RF waveform of low crest factor to give maximum power before the voltage is clamped at the values given. Typically a crest factor of 1.5 or less is achieved. When a combined mode output is required, the voltage output set via input 68C is constantly alternated between the value for desiccation or coagulation and the value for cutting or vaporisation, to form a blended waveform.

When the generator is first activated, the status of the control input 60I of the RF oscillator 60 (which is connected to the "on" time control circuit 70) is "on", such that the power switching device which forms the oscillating element of the oscillator 60 is switched on for a maximum conduction period during each oscillation cycle. The power delivered to the load 64 depends partly on the supply voltage applied to the RF oscillator 60 from the switched mode power supply 66 and partly on the load impedance 64. The voltage threshold for a desiccation output is set to cause trigger signals to be sent to the "on" time control circuit 70 and to the switched mode power supply 66 when the voltage threshold is reached. The "on" time control circuit 70 has the effect of virtually instantaneously reducing the "on" time of the RF oscillator-switching device. Simultaneously, the switched mode power supply is disabled so that the voltage supplied to oscillator 60 begins to fall. The operation of the generator in this way is described in detail in our European Patent Application No. 0754437, the disclosure of which is hereby incorporated by way of reference.

Figure 3:
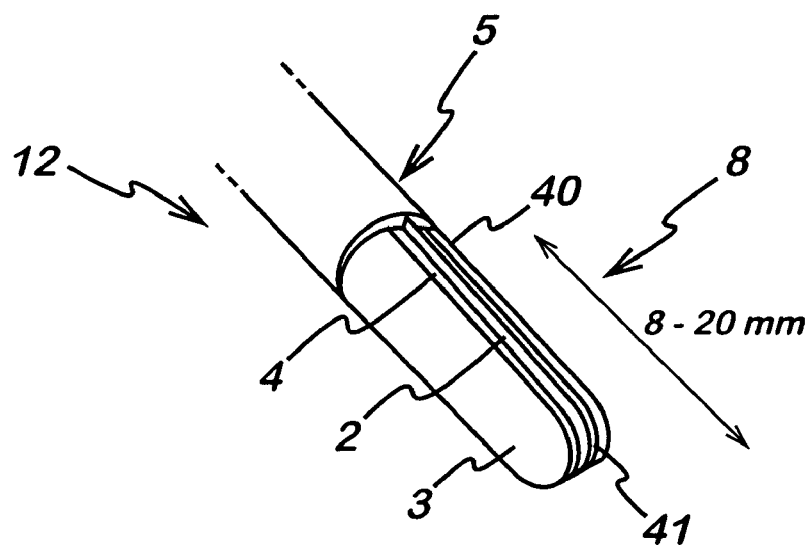
FIG. 3 is a schematic perspective view of an electrosurgical instrument used as a part of the system of FIG. 1.

FIG. 3 shows one possible design for the electrosurgical instrument 12. The instrument 12 comprises an instrument shaft 5 at the distal end of which is an electrode assembly shown generally at 8. The electrode assembly 8 comprises a central cutting electrode 2 disposed between two larger coagulation electrodes 3 and 40. Insulating layer 4 separates the cutting electrode 2 from the first coagulating electrode 3, while an insulating layer 41 separates the cutting electrode 2 from the second coagulation electrode 40. The cutting electrode 2 protrudes slightly beyond the two coagulating electrodes.

When the user intends the instrument to cut tissue, the generator applies a cutting RF waveform between the cutting electrode 2 and one or both of the two coagulating electrodes 3 and 40. Conversely, when the user intends the instrument to coagulate tissue, the generator applies a coagulating RF waveform between the two coagulating electrodes 3 and 40. The application of the blended RF waveform will be described with reference to the switching circuit shown in FIG. 4.

Figure 4:
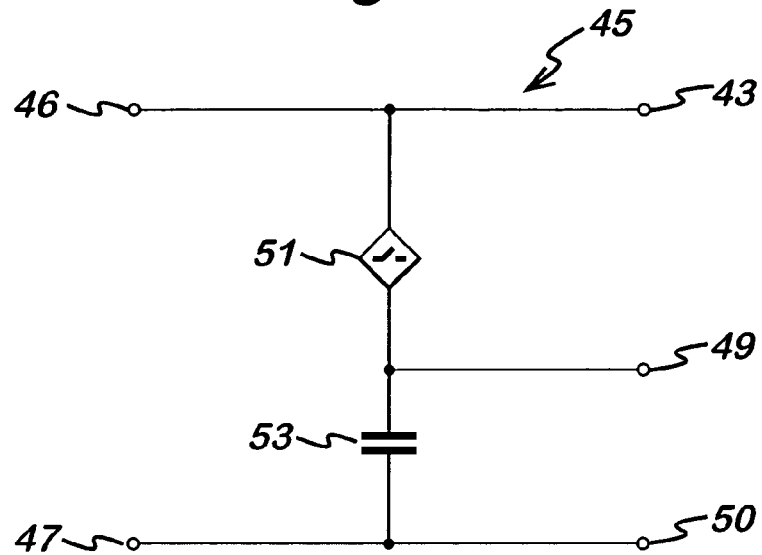
FIG. 4 is a schematic diagram of a switching circuit used in the system of FIG. 1, FIGS. 5A and 5B are circuit diagrams of two electronic switching devices for the switching circuit of FIG. 4.

FIG. 4 shows a switching circuit shown generally at 45 and comprising input connections 46 and 47 connected respectively to the two output lines 60C of the generator 10. Switching circuit 45 has three output connections 48, 49 and 50. Output connection 48 is connected to the cutting electrode 2 in the device of FIG. 3. Output connections 49 and 50 are respectively connected to the coagulating electrodes 3 and 40 in the device of FIG. 3. An electronic switch device 51 is connected between output connections 48 and 49. The switch 51 is capable of rapidly making and breaking the connection between the output lines 48 and 49. A capacitor 53 is connected between the output connections 49 and 50, the capacitor typically having a value of between 1 and 10 nF.

When the user actuates the pedals 16A or 16B to operate the instrument 12 in the blended mode, the generator supplies alternating bursts of the RF cutting and coagulating waveforms to the input connections 46 and 47. The switch device 51 operates synchronised with the alternating RF waveforms such that when that part of the waveform containing the cutting waveform is received, the switch device is open such that there is open circuit between the output connections 48 and 49. Thus the cutting RF waveform is supplied between cutting electrode 2 and coagulating electrode 40, via output connections 48 and 50 respectively. Conversely, when that part of the waveform containing the coagulating voltage is received across the input connections 46 and 47, the switching device 51 is closed such that output connections 48 and 49 are in electrical communication one with the other. Thus, during the coagulation part of the blended waveform, the waveform is supplied between the two coagulation electrodes 3 and 40, via output connections 49 and 50, with the capacitor 53 providing a potential difference therebetween.

Figure 5A:
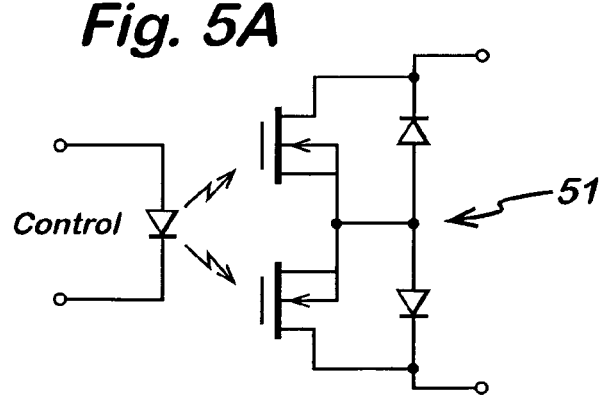

Switching device 51 may comprise an AC opto-relay such as the optically coupled dual FET arrangement shown in FIG. 5A. Another switching device providing isolation between control circuitry and the output lines is the combination of an AC bridge and a single MOSFET switch controlled via an isolating driver, a shown in FIG. 5B.

The above description is based upon the generator 10 controlling the blended mode waveform, and the switching device 51 opening and closing synchronously therewith. However, this does not have to be the case and the switching device can control the generator in order to determine the changeover between the cutting and coagulation RF waveforms.

Consider the switching circuit 45 as shown in FIG. 4. When the switching device 51 is in its open condition, the cutting waveform is supplied across output connections 48 and 50. When the switching device 51 closes, the cutting waveform is initially supplied between the output connections 49 and 50, separated by the capacitor 53. This causes the current delivered by the generator to rise rapidly such that the current limiting circuitry within the generator operates to reduce the power being delivered, such that the waveform rapidly converts to an RF waveform typical for coagulation. The effect of the current limiting circuitry within the generator is that the closing of the switching device 51 causes the waveform being delivered to be transformed, almost instantaneously, from a cutting waveform to a coagulating waveform. Conversely, when the switching device 51 opens again, the generator ceases to be current limited, and the waveform once again rapidly reverts to being a cutting RF waveform. In this way, the opening and closing of the switching device 51 toggles the generator between its cutting and coagulating modes, producing the blended waveform which is supplied to the electrodes of the instrument 12.

Figure 6:
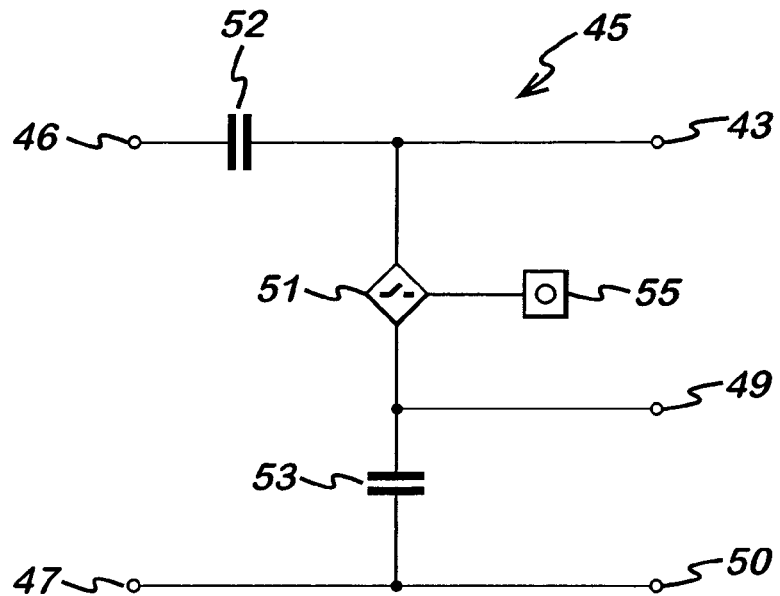
FIG. 6 is a schematic diagram of an alternative embodiment of switching circuit which can be used in the system of FIG. 1.

FIG. 6 shows an alternative embodiment of switching circuit, which can be employed if the generator 10 is not a current limited generator, or if it is desired not to use the current limiting features of the generator. The switching circuit of FIG. 6 is almost identical to that of FIG. 4, the main difference being the addition of an additional capacitor 52 in series with the input connection 46. The capacitor 52 typically has a value one half of that of capacitor 53, such that the voltage delivered across output connections 49 and 50 is divided down to a level typically used for coagulation without reducing the power output of the generator 10. In this way a cutting RF waveform is delivered between output connections 48 and 50 when the switching device 51 is open, and a coagulating RF waveform is delivered between output connections 49 and 50 when the switching device is closed.

Figure 7:
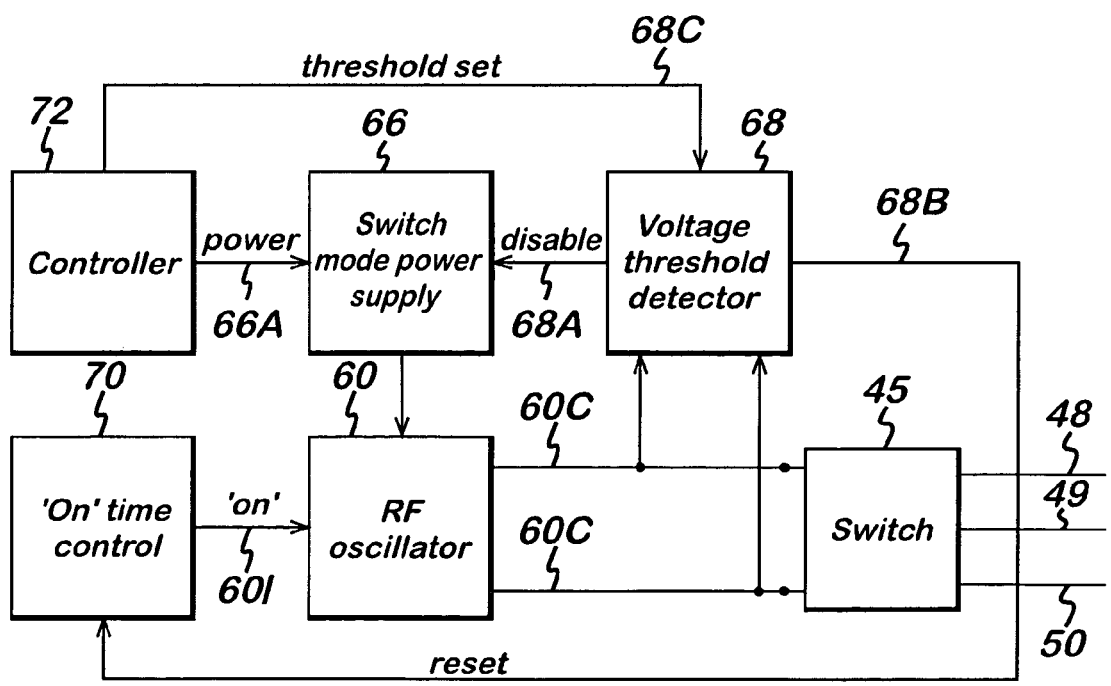
FIG. 7 is a block diagram of a generator in accordance with FIG. 2, incorporating a switching circuit in accordance with FIG. 4, FIGS. 8A to 8C are diagrams illustrating techniques for adjusting a blend switching ratio, FIGS. 8A and 8C being circuit diagrams of alternative ratio adjusting devices and FIG. 8B being a waveform diagram illustrating the operation of the device of FIG. 8A.

Switching circuit 45 can be provided within the electrosurgical instrument 12, or within the output stage of the generator 10 as shown in FIG. 7. Wherever the switching circuit 45 is located, the switching device can be provided with an adjustment device 55, (as shown in FIG. 6) operable by the user of the system in order to adjust the timing of the switching device. By operating the adjustment device 55, the user is able to alter the ratio between that part of the blended RF waveform which is a cutting waveform, and that part which is a coagulating waveform. Whether the adjustment device 55 is located on the instrument 12 or the generator 10, the user of the system can vary the waveform so as to increase or decrease the coagulating component of the blended waveform with respect to the cutting component, and vice versa. This gives considerable flexibility to the electrosurgical system in terms of its use as a simultaneous cutting and coagulation device, with user-operable control of how much coagulation is provided.

Figure 5B:
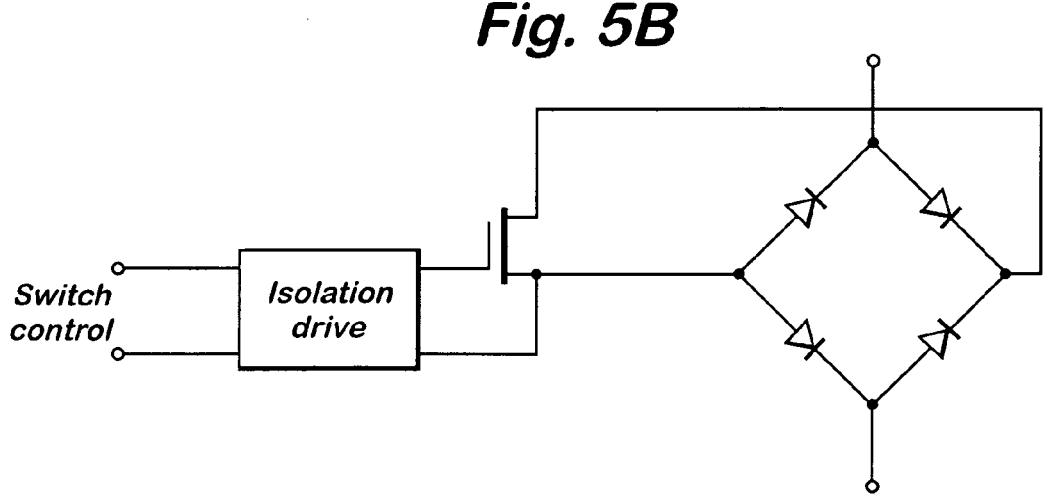

As in the arrangement described above in FIG. 4, the switching device 51 of the alternative switching circuit of FIG. 6 may be as shown in FIG. 5A or FIG. 5B, the driving signal being obtained from a source associated with the switching device itself or from control circuitry within the generator which controls other generator functions.

Figure 8A:
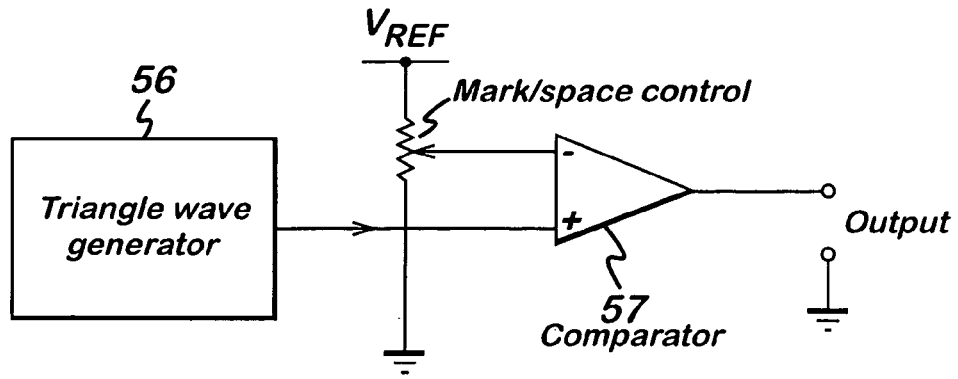
Figure 8B:
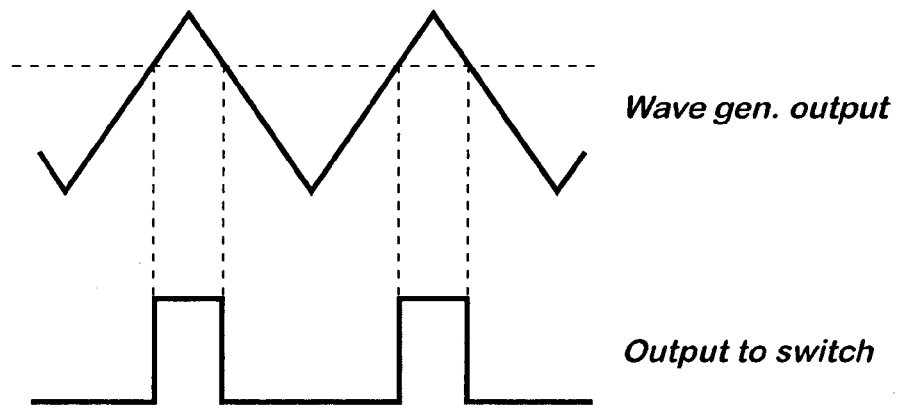
Figure 8C:
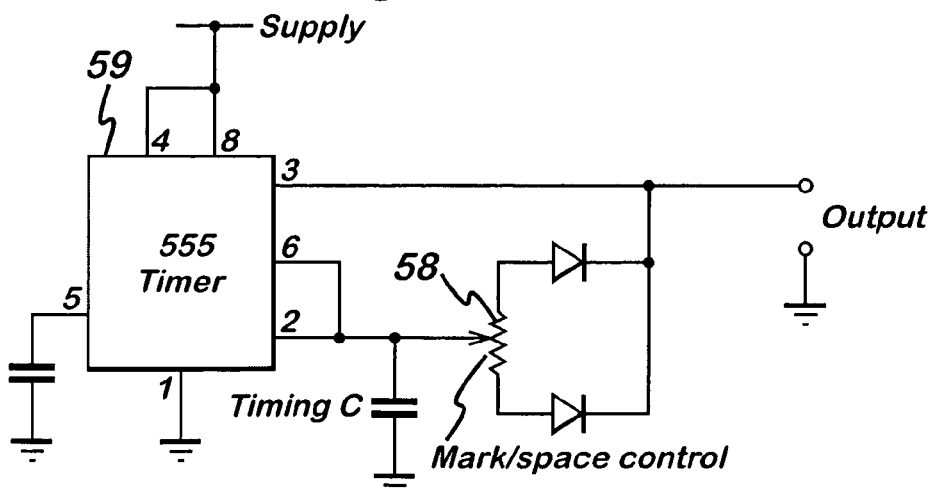

Various circuits for implementing the adjustment device 55 will be apparent to those skilled in the art. An example of a circuit in which a blended mode waveform is generated by elements associated with the switching device and has a variable mark-to-space ratio is shown in FIG. 8A. In this case, the output of a triangular wave generator 56 is compared in a comparator 57 with a user-adjustable reference voltage to produce a square wave of the switching device 51 (FIG. 6). Another circuit generating an adjustable blended mode switching device control signal is shown in FIG. 8C. Here, a user-operable potentiometer 58 is coupled with a timer circuit 59 using a 555 i.c.

FIG. 9 shows an alternative generator system in which two RF source circuits 74 and 74' are employed. Source circuit 74 comprises RF oscillator 60 and its associated power supply and control elements. The source circuit is as described with reference to FIG. 2, and like elements are given the same reference numerals as in FIG. 2. The second source circuit 74' comprises a second RF oscillator 60', along with a second controller 72', power supply 66', voltage threshold detector 68' and on time control circuit 70'. FIG. 9 shows the source circuit 74' as having its own dedicated version of each of these units, although it is feasible that certain of them (such as the power supply 66' and controller 72') could be shared with the source circuit 74. The voltage threshold detector 68 is set such that the output connections 60C from source circuit 74 provide an output power waveform having a cutting RF waveform, while the voltage threshold detector 68' is set such that the output connections 60C' from source circuit 74' provide an output power waveform having a coagulating RF waveform. The second oscillator 60' operates at a different frequency from that of oscillator 60.

A common output stage 73 is provided for both source circuits 74 and 74'. Output connections 60C from source circuit 74 are connected to input connections 46 and 47 of the output stage 73, while output connections 60C' from source circuit 74' are connected to input connections 46' and 47' of the output stage respectively. Within the output stage 73, input connections 47 and 47' are both connected to output connection 49, while input connection 46 is connected to output connection 48, and input connection 46' to output connection 50. The result of this arrangement is that the cutting RF waveform from source circuit 74 is delivered between output connections 48 and 49 and hence to one pair of electrodes on the electrosurgical instrument 12. Simultaneously, the coagulating RF waveform from source circuit 74' is delivered between output connections 49 and 50 and hence to a different pair of electrodes of the instrument 12. Thus the electrosurgical instrument 12 is able simultaneously to cut and coagulate tissue by virtue of the two different frequency waveforms. As before, the advantage is that the cutting waveform and the coagulating waveform, whether they be applied simultaneously or in an alternating blended waveform, are delivered to different pairs of electrodes of the electrosurgical instrument. The design of these electrodes can therefore be optimised, depending on whether they are intended to cut or coagulate tissue.

Figure 10:
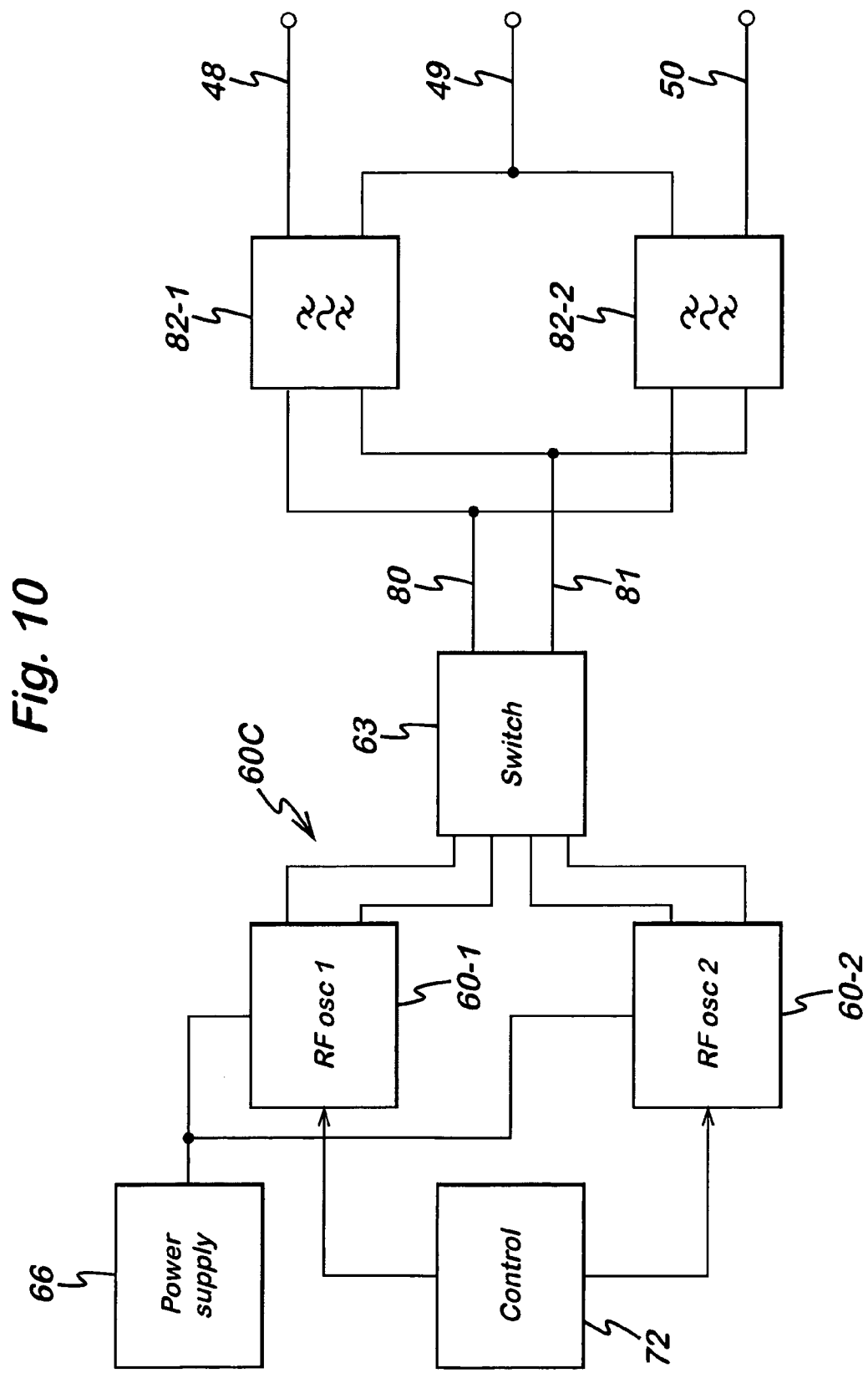
FIG. 10 is a block diagram of a further alternative system in accordance with the invention.

Referring to FIG. 10, in an further alternative generator and instrument combination, two RF power oscillators 60-1 and 60-2 are powered from a common power supply 62 and are controlled by a common controller 72 to produce on respective output lines 60C an RF power waveform suitable for cutting and an RF power waveform suitable for coagulation. These waveforms may be fed to a switching circuit 63 for selecting the power signal from one oscillator 60-1 or the other oscillator 60-2 according to inputs from, for instance, foot switches, the selected power waveform being transmitted on output connections 80, 81. In a blended mode, the switch is operated repeatedly at a predetermined rate to produce a blended output power waveform across connections 80, 81. The power oscillators 60-1, 60-2 are operated at different frequencies, and the respective cut and coagulation waveforms are fed to the required electrodes by feeding the power waveform on output connections 80, 81 to tuned circuits 82-1 and 82-2 tuned to the different frequencies. The outputs of the tuned circuits are coupled via electrode lines 48, 49 and 50 to the respective electrodes of the electrosurgical instrument. In this way, the cutting waveform from oscillator 60-1 is fed to a cutting electrode 48 and a common electrode 49, whereas the coagulation waveform from oscillator 60-2 is fed to a coagulation electrode 50 and the common electrode 49.

In the embodiment shown in FIG. 10, the connection between the electrosurgical generator and the electrosurgical instrument is typically provided by output connections 80 and 81, but the apportionment of circuit blocks between the generator and the instrument may be varied.

Figure 11B:
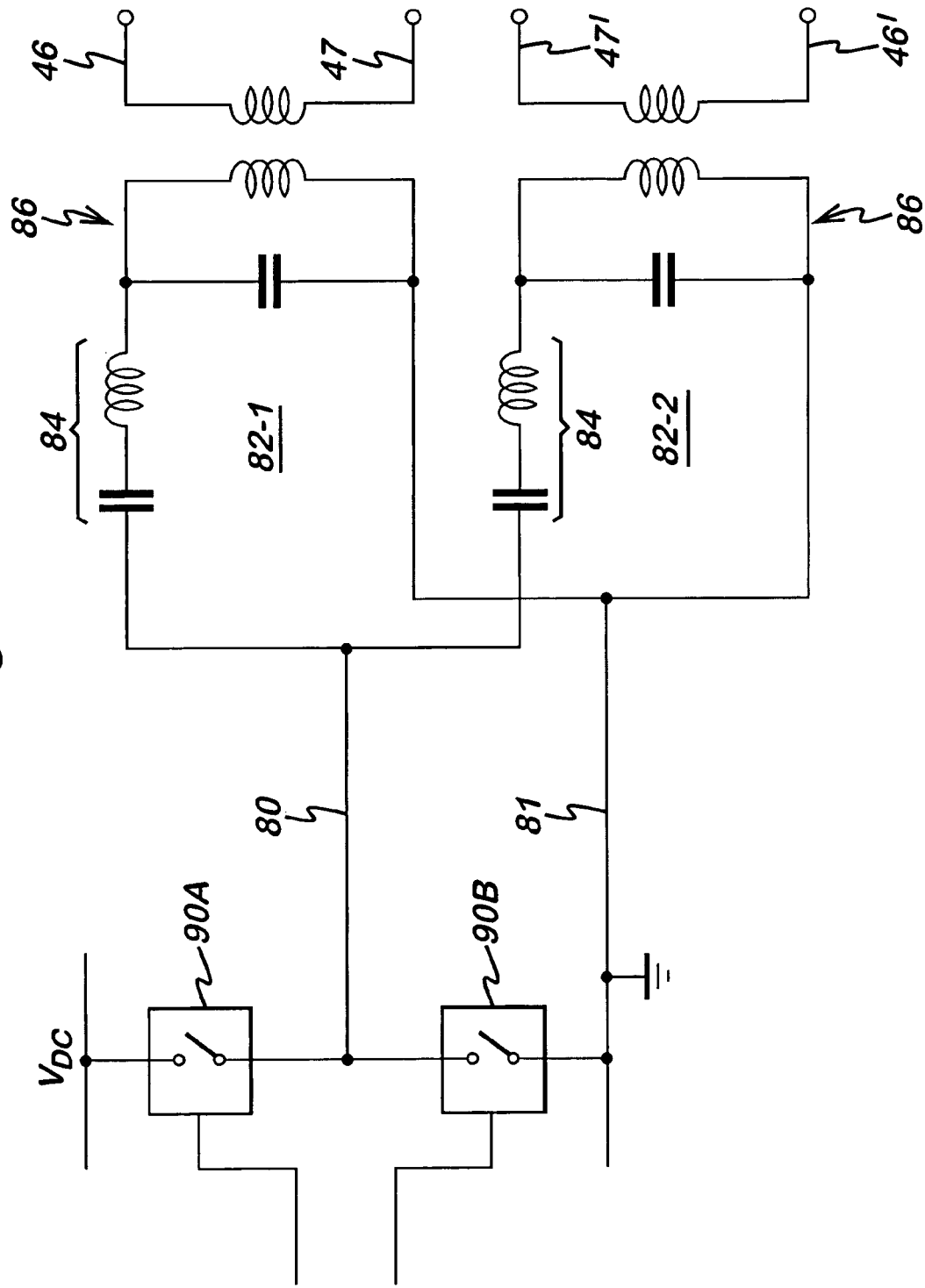

Further embodiments are shown in FIGS. 11A and 11B. Like the embodiment of FIG. 9, these embodiments dispense with the need for a signal routing switch or switching circuit.

Referring to FIG. 11, there are provided two tuned circuits 82-1 and 82-2 (as in FIG. 10), tuned to different frequencies. Each has a series-resonant inductor-capacitor pair 84 and a parallel-resonant inductor-capacitor pair 86, the latter being transformer coupled to output connections 46 and 47 on the one hand and 46' and 47' on the other hand. As in the embodiment of FIG. 10, each tuned circuit has two inputs, one of which is connected to a generator output connection 80 and the other of which is connected to a generator output connection 81. In this embodiment, the generator has an output stage comprising RF switches arranged in two oppositely acting push-pull pairs 90A, 90B and 91A, 91B. Typically these switches comprise power MOSFETS. Each switch 90A, 90B, 91A, 91B is connected to driver inputs 92, 93, as shown, which receive an RF drive signal which, for producing on the output connections 80, 81 an output having a cut waveform is at one RF frequency, and for producing a coagulation output on the output connections 80, 81, has a different RF frequency, these frequencies being, respectively, the resonant frequency of, the resonant combinations 84, 86 of the first tuned circuit 82-1 and, the resonant frequency of the corresponding resonant combinations of the other tuned circuit 82-2. As described above, the RF switches 90A, 90B, 91A and 91B of the generator output stage may be driven according to, for instance, a footswitch control to produce a cut output or a coagulation output. Again, additionally, a blended output may be produced in which the RF frequency alternates constantly between the two resonant frequencies of the tuned output circuits.

The embodiment of FIG. 11B is a modification of that of FIG. 11A, in which the generator output stage has a single push-pull pair of RF switches 90A, 90B and in which the tuned circuits each have one input connected to the junction between the switches 90A, 90B and the other input connected to ground.

Figure 12:
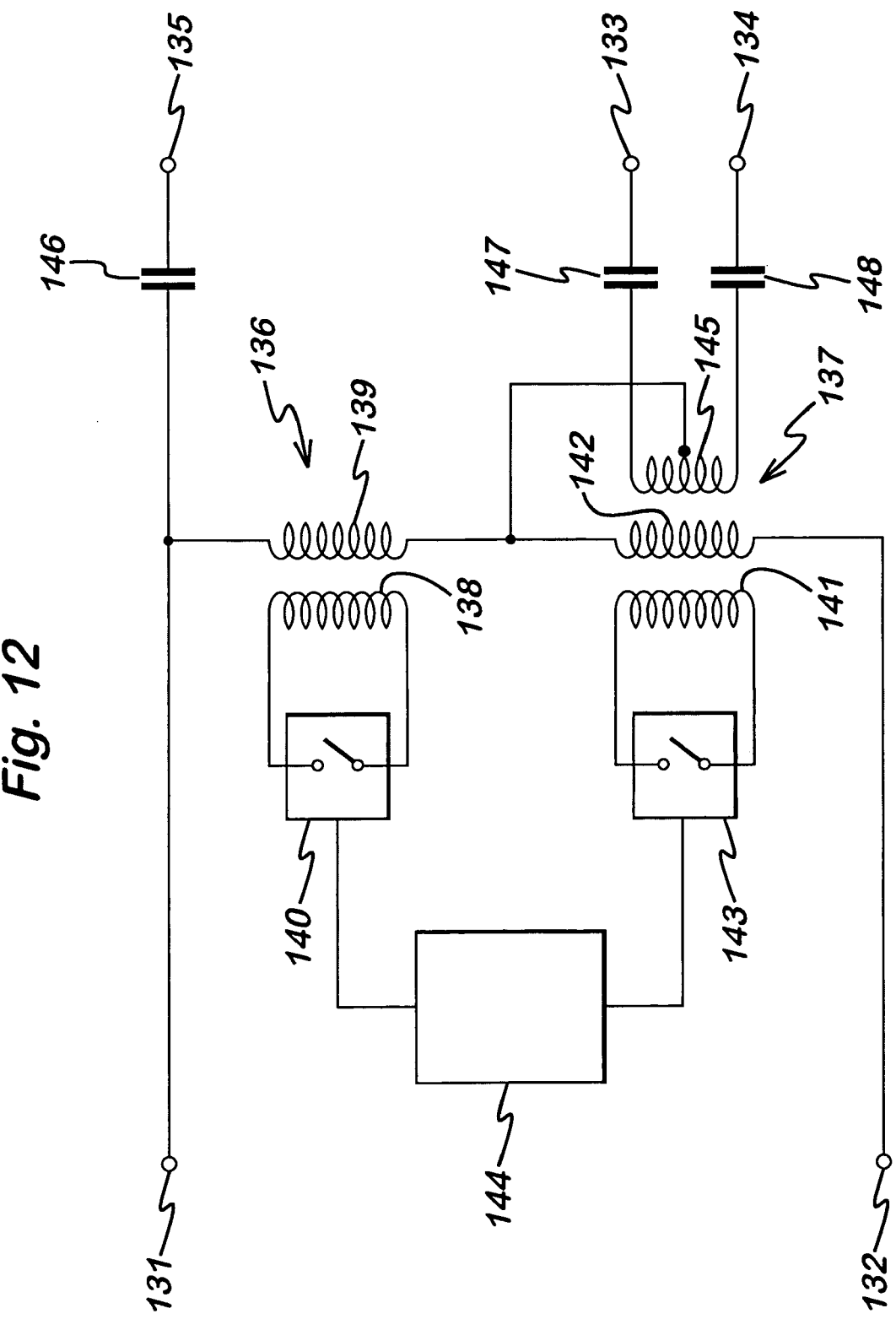
FIGS. 12 and 13 are block diagrams of further alternative systems in accordance with the invention.

A further embodiment of generator circuit is shown in FIG. 12, in which the cut and coag outputs are connected in series across the switching circuitry. Input connections 131 and 132 are connected to the output of the generator, and output connections 133 and 134 to the coag electrodes of the electrosurgical instrument 12. Output connection 135 is connected to the cutting electrode of the electrosurgical instrument 12.

Between the input connections 131 and 132 there is a bridge circuit comprising a first transformer 136 and a second transformer 137. First transformer 136 comprises primary winding 138 and secondary winding 139. A first switch element 140 is provided in parallel with primary winding 138. Second transformer 137 comprises primary winding 141 and secondary winding 142. A second switch element 143 is provided in parallel with primary winding 141. Switch elements 140 and 143 are operated by control unit 144. The secondary windings 139 and 142 are connected in series across the input connections 131 and 132, the junction between the two windings 139, 142 constituting a bridge output.

The second transformer 137 is a step-down transformer in which the secondary winding 142 is itself the primary to a further, a center-tapped, secondary winding 145 connected across the output connections 133 and 134. An isolation capacitor 146 is provided between the bridge circuit and the cutting output connection 135, and further isolation capacitors 147 and 148 between the bridge circuit and the coagulation output connections 133 and 134.

The operation of the circuit is as follows. For a predetermined period, control unit 144 operates switch element 143 to close and short circuit the primary winding 141 of the second transformer 137. In this condition, with the transformer secondary 141 effectively short-circuited, the output of the generator is directed between the output connection 135 and both of the output connections 133 and 134. This has the effect of energizing the cutting electrode of the electrosurgical instrument 12 with an RF output voltage with respect to the coagulating electrodes thereof, which effectively act as return electrodes for the electrosurgical cutting operation.

At the end of the predetermined period, the control unit 144 operates to open switch 143 and then close switch 140 to short circuit the primary winding 138 of the first transformer 136. There is a short predetermined delay between the opening of switch 143 and the closing of switch 140 to ensure that both switches are never closed at the same time (as this would short circuit the output connections of the generator). With switch 140 closed, the first transformer 136 is effectively short-circuited, and the output of the generator is directed entirely to the second transformer 137. The second transformer is a step-down transformer, and provides a lower voltage signal between the output connections 133 and 134. This has the effect of energizing the first and second coagulating electrodes of the electrosurgical instrument 12 so as to produce an RF coagulating voltage between them.

After a predetermined time, the control unit 144 opens switch 140 and then closes switch 143, reverting to the condition initially described in which a cutting voltage is delivered to the cutting electrode of the electrosurgical instrument 12. By constantly alternating between the two conditions herein described, the circuit provides a rapidly alternating cut and coagulation ("coag") waveforms signal to an electrosurgical instrument connected thereto. In this way, the instrument is able to cut tissue as previously described, while simultaneously coagulating the tissue in order to curtail bleeding.

Figure 13:
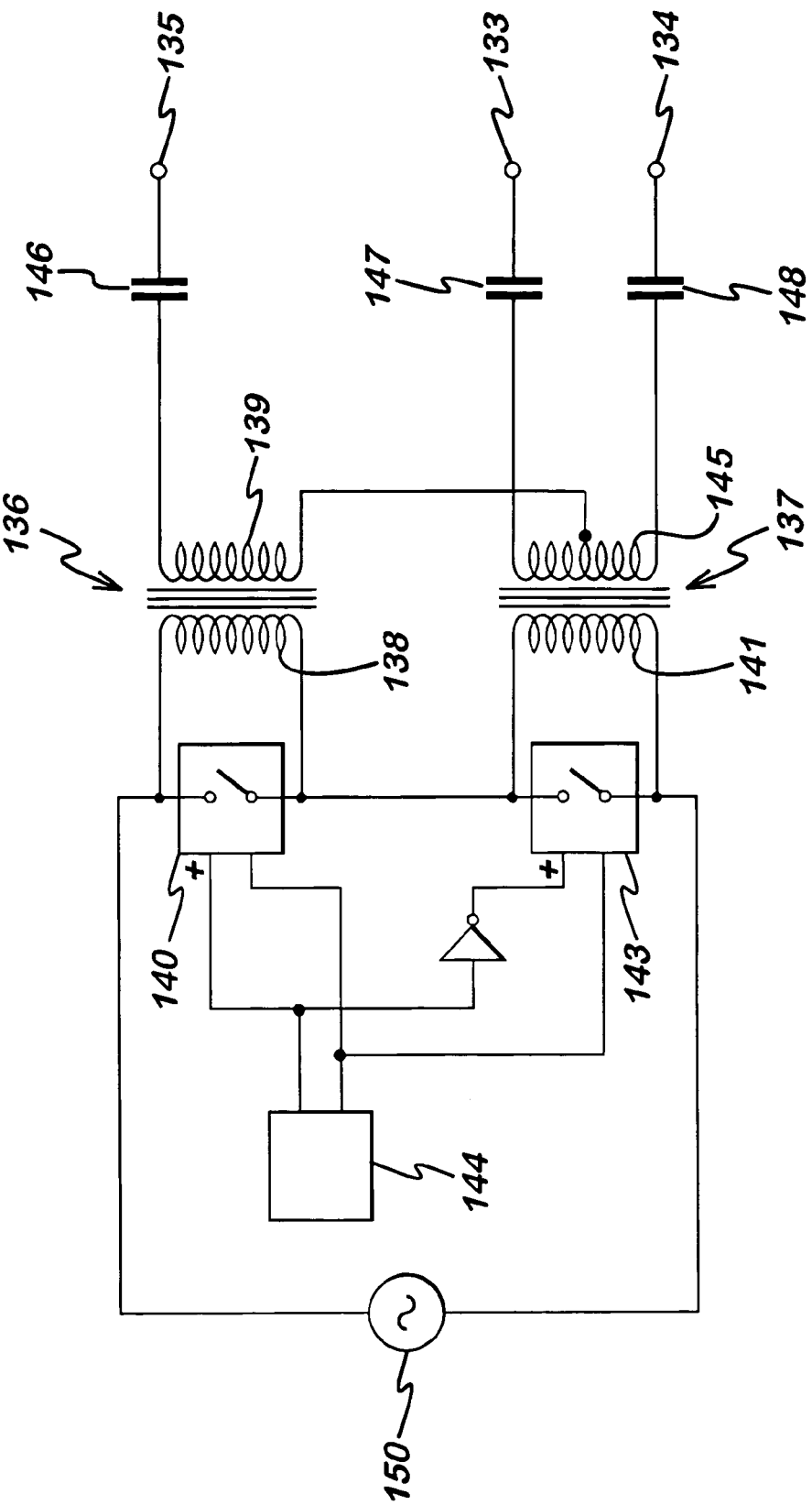

FIG. 13 shows an alternative embodiment, in which like elements are designated by like reference numerals. Whereas the arrangement of FIG. 12 is particularly suitable for a switching circuit in a unit separate from the generator, the arrangement of FIG. 13 is more suitable for switching circuitry which is integral with the generator. Instead of the secondary windings 139 and 142 being connected across the generator as in FIG. 12, in the arrangement of FIG. 13 the switching elements 140 and 143 across the primary windings 138 and 141 are themselves connected directly in series across a generator 150. In FIG. 13, the second transformer 137 is shown as a simple primary winding 141 and secondary winding 145, without the additional isolation provided by the two-stage transformer shown in FIG. 12. The operation of the circuit of FIG. 13 is substantially as described with reference to FIG. 12, with the control unit 144 causing switches 140 and 143 to open and close in a reciprocal fashion. When switch 140 is closed, shorting primary winding 138, a coagulating signal is supplied between output connections 133 and 134. Alternatively, when switch 143 is closed, shorting primary winding 141, a cutting signal is supplied between the output connection 135 and the connections 133 and 134.

Figure 14A:
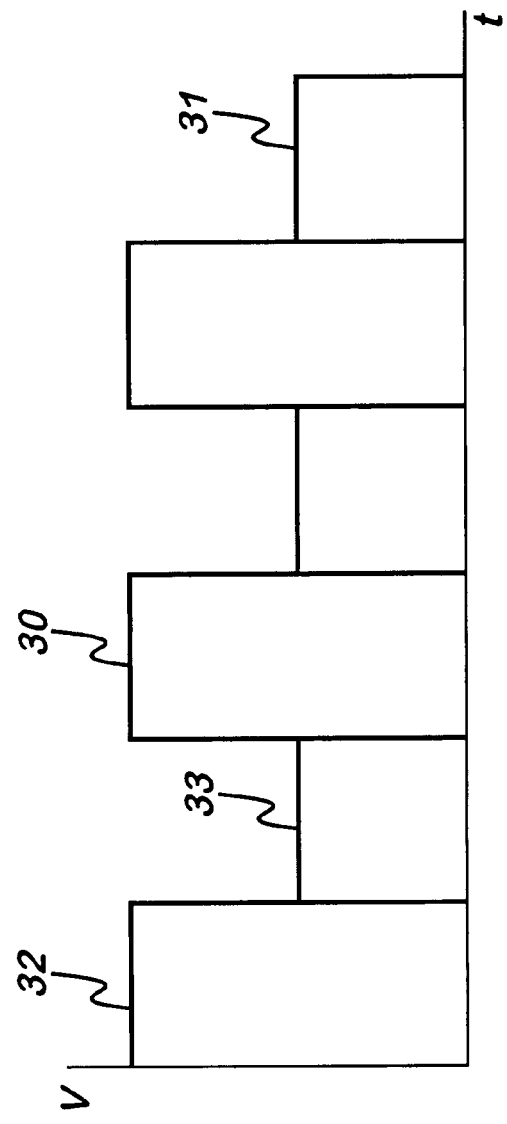
FIGS. 14A and 14B are waveform diagrams showing different blend waveforms capable of being produced by a generator in accordance with the invention.

FIG. 14A shows a first blended output waveform sequence which comprises a constantly alternating combination of a cut waveform 30 and a coag waveform 31. The cut waveform 30 is limited to a first voltage threshold 32, while the coag waveform 31 is limited to a second (lower) voltage threshold 33. The cut waveform 30 is supplied for 50% of the duty cycle, and the coag waveform 31 is supplied for the remaining 50% of the duty cycle. This output waveform sequence produces a tissue effect which simultaneously cuts and coagulates tissue.

Figure 14B:
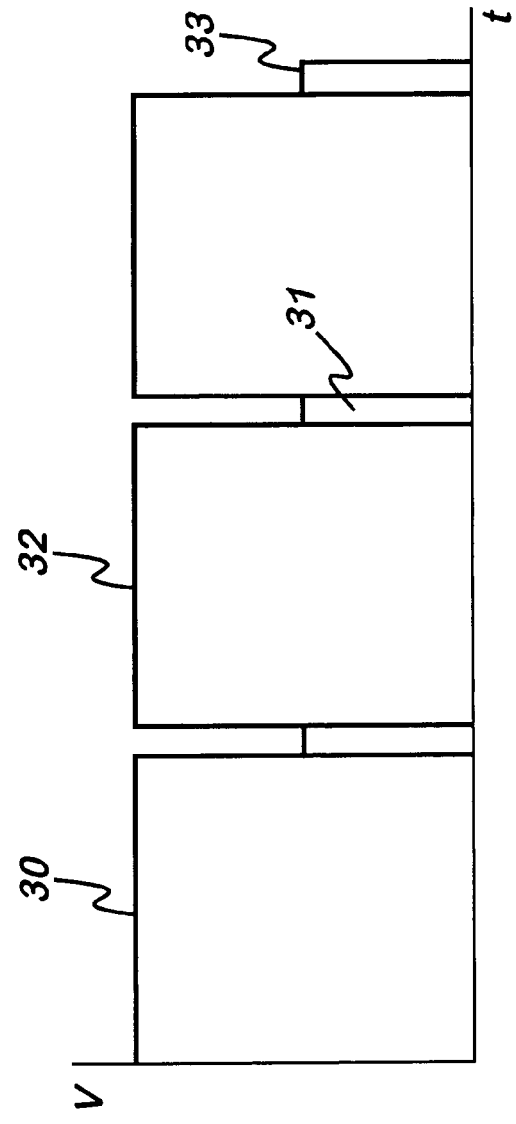

FIG. 14B shows an alternative blended output waveform sequence, again alternating constantly between a cut waveform 30 and a coag waveform 31, each limited to voltage thresholds 32 and 33 respectively. However, in the output waveform sequence of FIG. 14B, the cut waveform 30 is supplied for 90% of the duty cycle, and the coag waveform 31 is supplied for only 10% of the duty cycle. This output waveform sequence cut tissue more effectively than the waveform of FIG. 14A, but less of a coagulative effect on the tissue being treated.

Figure 15:
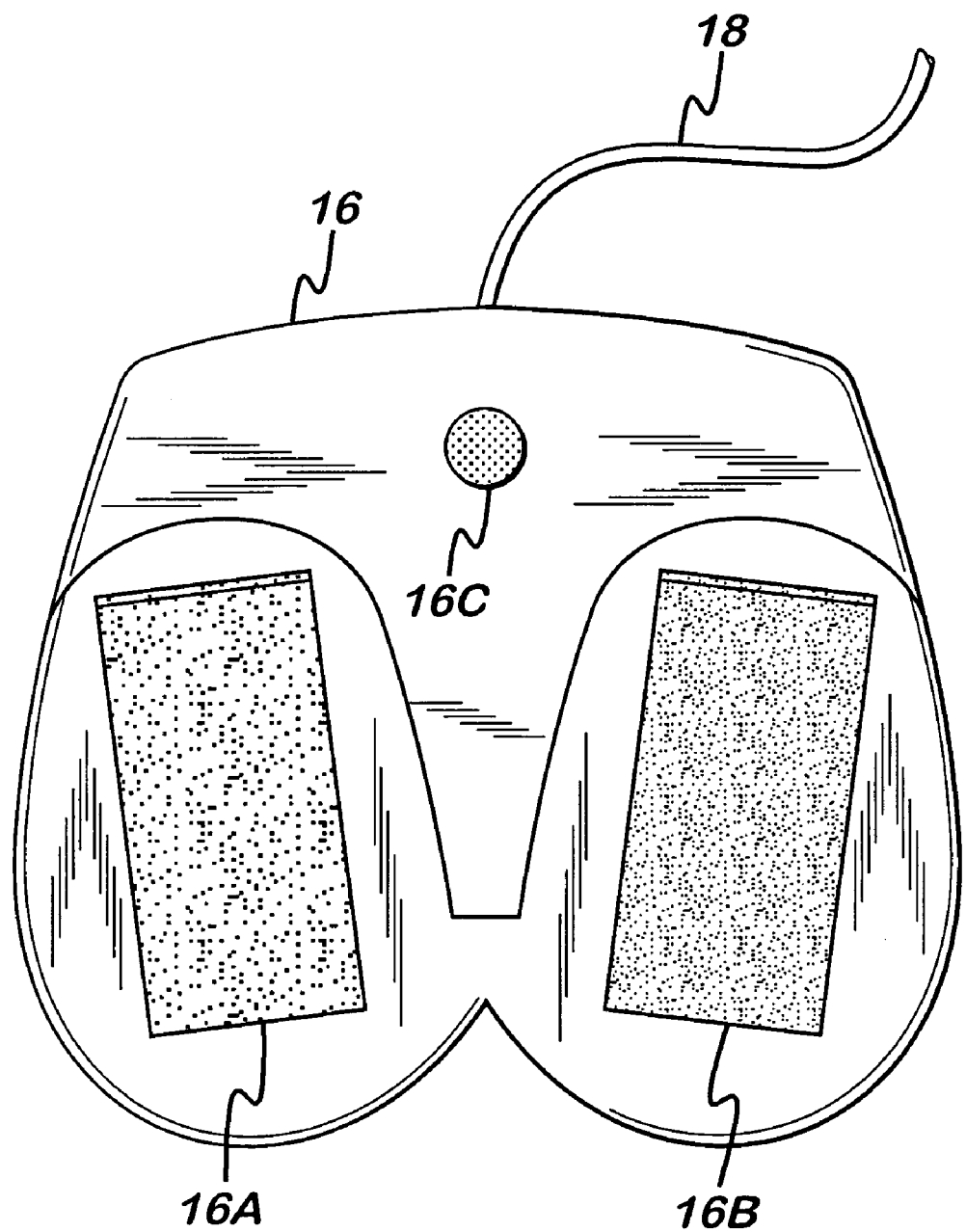
FIG. 15 is a schematic view of a footswitch used as a part of an electrosurgical system in accordance with the present invention.

The blended waveforms of FIGS. 14A and 14B are two preset settings for the blended output waveform sequence of a generator system according to the present invention, and can be selected or adjusted by the use of a footswitch as shown in FIG. 15, which footswitch is entirely conventional. The footswitch 16 has two pedals 16A and 16B, the pedal 16A being commonly known as the cut pedal (and typically being coloured yellow), and the pedal 16B being commonly known as the coag pedal (and typically being coloured blue). A third pedal 16C is provided as a mode selection pedal (this pedal typically being of a different shape and size to the other two pedals, and commonly coloured black). The operation of the generator system will now be described with reference to these pedals, and to the diagram of FIG. 16.

If the surgeon is using the electrosurgical instrument connected to the generator merely to coagulate tissue, the actuation of the coag pedal 16B will cause a 100% coag waveform to be supplied to the instrument. However, when the surgeon wishes to use the instrument to cut tissue, the cut pedal 16A is actuated. When the cut pedal is actuated, the generator supplies a waveform to the instrument in accordance with a predetermined start setting, in this case a 100% coag waveform as shown at "A". As subsequent pulses of energy are supplied to the instrument, the waveform changes according to a predetermined progression, until at "B" the waveform is 50% cut and 50% coag. After time $t_1$ the waveform has progressed to its end setting as shown at "C", which in this instance is a waveform constituted by 90% cut and 10% coag waveforms. This end setting will be applied to the instrument until the cut pedal 16B is released.

This progression of the waveform for a start setting to an end setting has several advantages for the surgeon. Firstly, when using the instrument to cut through thick tissue, bleeding often occurs. This cannot always be compensated for by coagulating thick tissue prior to cutting, as there is the risk that in order to ensure that the entire tissue is coagulated, some of the tissue will become "over-coagulated" and be desiccated. Desiccated tissue is not receptive to RF energy, and so the subsequent cutting of the tissue will not be effective. Thus, bleeding is often associated with the cutting of thick tissue. In the present arrangement, the instrument maintains an element of coagulation, especially at the start of the process. Thus, if the surgeon encounters bleeding during the electrosurgical cut, the surgeon releases and then re-activates the cut pedal 16B. This re-sets the progression to point "A" in FIG. 16, with a high degree of coagulation in the start setting.

Secondly, the increasing proportion of the cut waveform ensures that the cutting of tissue is effective as soon as it is feasible to occur. Maintaining at least a 10% proportion of the coagulation waveform ensures that coagulation continues to occur as the instrument moves through the tissue.

The time taken for the generator to progress from the start setting to the end setting may be varied depending on the type of instrument connected to the generator, and/or the type of tissue typically treated by that instrument. The progression time may be a factory setting, or may be user adjustable using the mode adjustment pedal 16C. The progression time is typically of the order of 7.5 seconds, although progression times of as short as 0.5 seconds or as long as 10 seconds may be used in appropriate circumstances.

Figure 16:
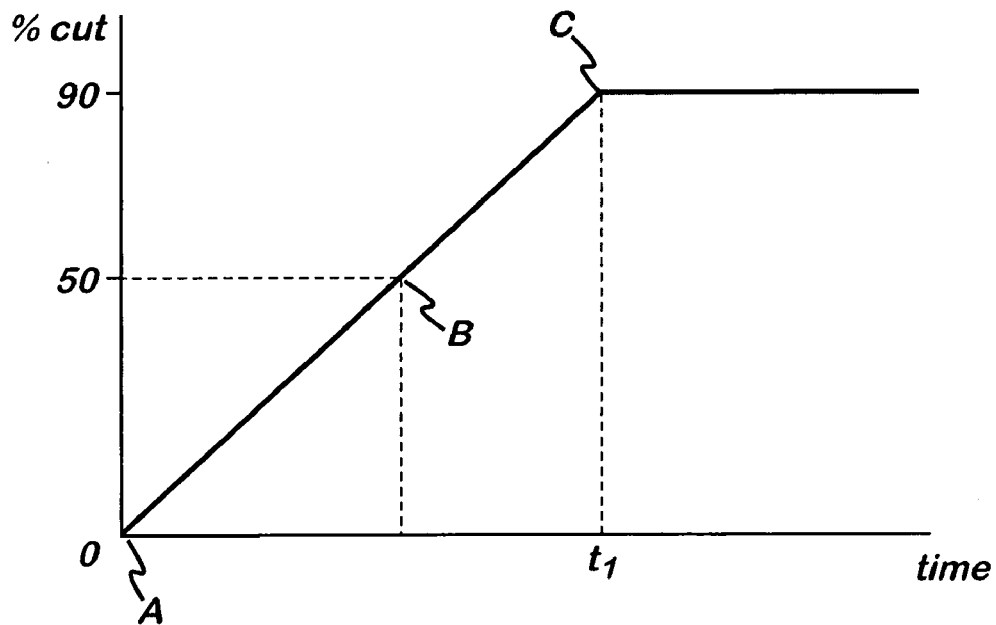
FIGS. 16 and 17 are diagrams illustrating the adjustment of the generator in accordance with the invention.
Figure 17:
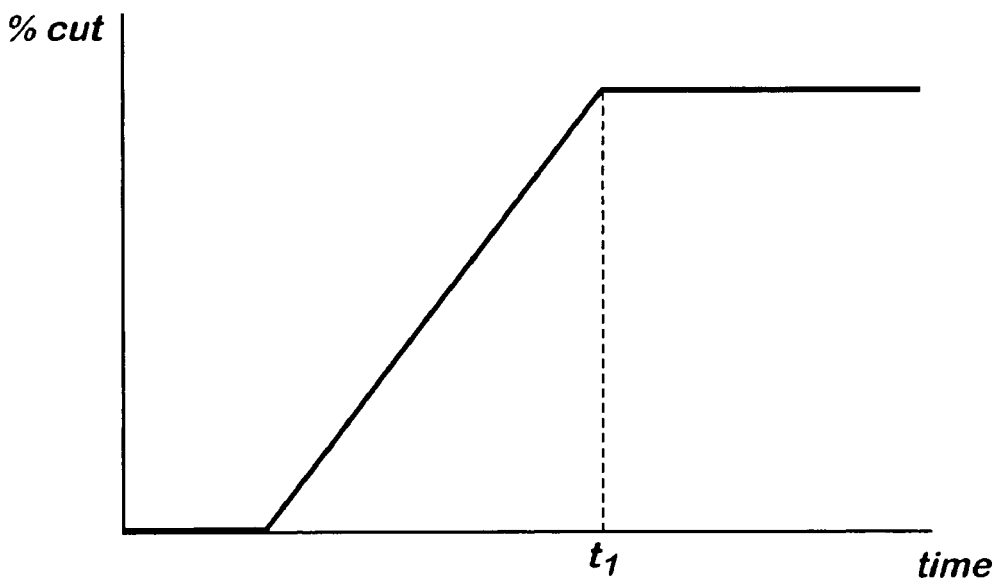

The progression from the start setting to the end setting may not necessarily be an even progression as shown in FIG. 16. For example, the waveform may remain with a 100% coag content for a predetermined time (say 1.5 seconds) before progressing to the end setting of 90% cut and 10% coag. This is the situation shown in FIG. 17. The skilled man will appreciate that different progressions from the start setting to the end setting will be possible, depending on the type of operation being undertaken.

Figure 18:
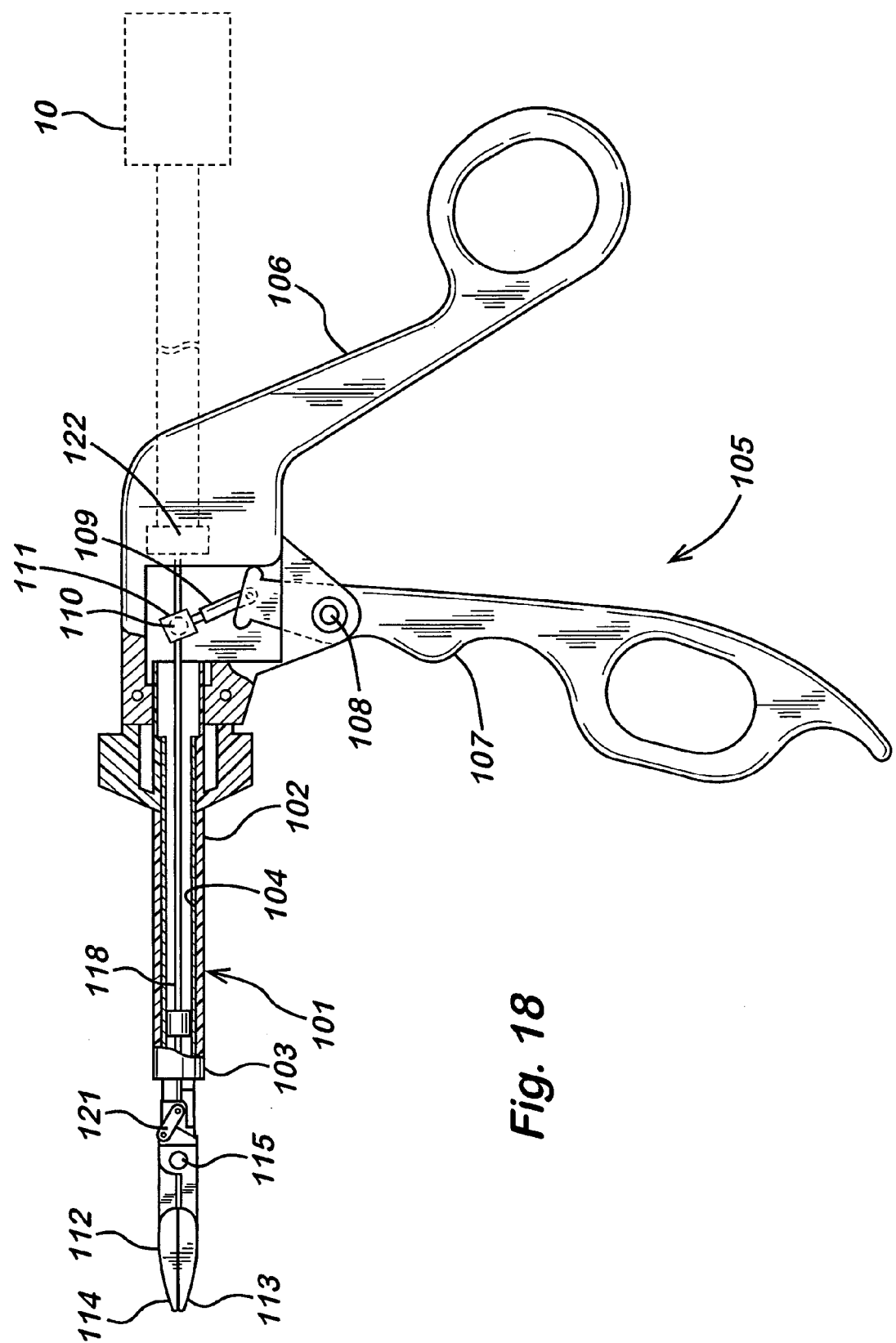
FIG. 18 is a schematic sectional view of an alternative electrosurgical instrument used as part of the system of FIG. 1.
Figure 21:
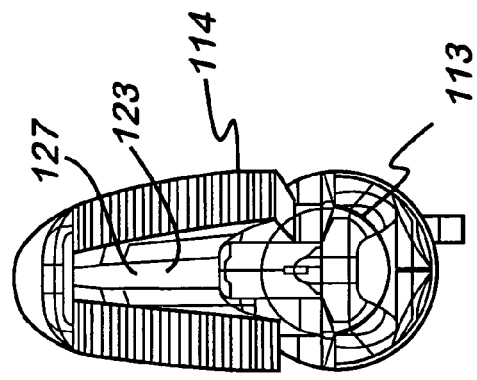
FIG. 21 is an end view of the jaw assembly of FIG. 19.

FIGS. 18 to 22 show an alternative type of instrument that can be used in conjunction with the previously described electrosurgical generator. Referring to FIG. 18, a bipolar forceps device includes an elongated tubular shaft 101 with a proximal end 102, distal end 103, and a lumen 104 which extends for the entire length of the tubular member. At the proximal end 102 of the tubular member 101 is a scissors-type handle assembly 105 with a first handle 106 and a second handle 107. The second handle 107 is pivotable with respect to the first, about pivot pin 108. In a known design of actuation mechanism, the second handle 107 has a pin 109 affixed to the top thereof, such that movement of the handle causes a corresponding movement to a sphere 110 supported in a U-shaped cradle 111.

Figure 22:
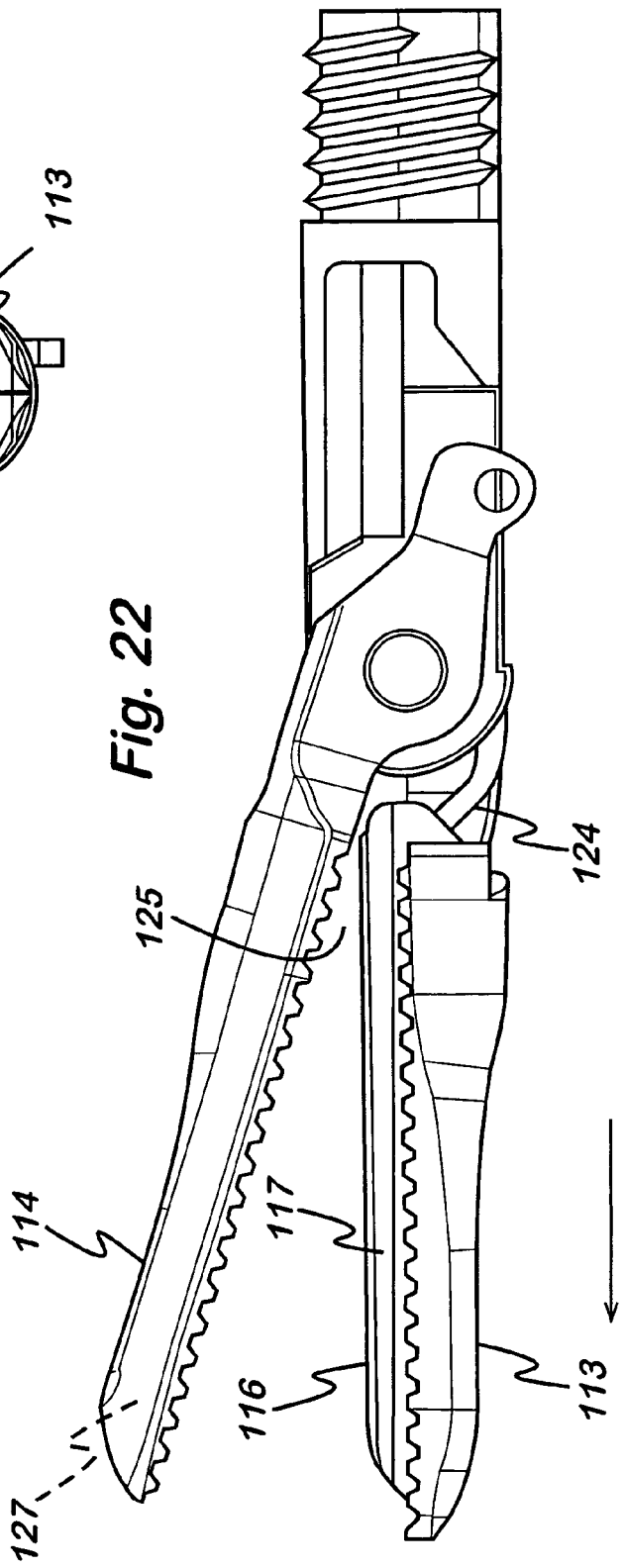
FIG. 22 is a side view of the jaw assembly of FIG. 19.

Fitted into the distal end 103 of the tubular member 101 is a forceps jaw assembly 112, more particularly shown in FIG. 19. The jaw assembly 112 comprises a first jaw member 113 and a second jaw member 114, pivotally joined to each other by an insulated rivet 115. Jaw member 113 is provided with a cutting electrode 116, isolated from jaw member 113 by a ceramic insulator 117. As shown in FIG. 20, three rigid electrically conductive rods 118, 119 and 120, each covered with a layer of electrical insulation, extend through the lumen 104 of the tubular member 101. The rods 118, 119 are pivotally connected to the respective jaw members 113, 114 by rigid links 121, whilst rod 120 is connected by means of a wire 124 (as best shown in FIG. 22) to the electrode 116. The proximal ends of the rods 118, 119 and 120 extend from the tubular member through the sphere 110 and terminate in a connector 122, by which means the device can be attached to the electrosurgical generator 10.

As shown in FIG. 19, the cutting electrode 116 is in the form of an elongate rail, extending along the length of the jaw member 113. The rail 116 is mounted on the ceramic insulator 117 such that it is insulated from the jaw member 113. The rail 116 is typically 100 microns in width, and protrudes from the ceramic insulator 117 by a distance of approximately 50 microns. When the jaw assembly 112 is in its closed position, the rail 116 is received in a corresponding longitudinal recess 123 in the jaw member 114, best shown in FIG. 21. A compressible strip 127 of insulting material is provided in the recess 123.

The operation of the device will now be further described. When tissue is to be cut, the jaw assembly 112 is brought adjacent the tissue to be cut, with the jaw assembly in its open position and the tissue positioned in the nip 125 of the jaw assembly. A cutting waveform from the electrosurgical generator 10 is supplied via the rod 120 to the cutting electrode 116, and the forceps device is moved longitudinally in the direction of the arrow shown in FIG. 22. Tissue bridging the cutting electrode 116 and one or both of the jaw members 113 and 114 is severed by the electrosurgical waveform as the device is translated longitudinally, thereby forming a longitudinal cut line in the tissue. The jaw assembly is maintained in its open position throughout this process, defining the nip 125 in which the tissue is constrained.

The device can also be used to coagulate tissue, in a more conventional manner, using the jaw assembly in its closed position. The jaw assembly is closed, capturing tissue between the jaw member 113 and the jaw member 114. The cutting rail 116 is received in the recess 123 and, without the electrosurgical cutting waveform previously described, does not have a cutting effect on the tissue therebetween. A coagulating waveform from the electrosurgical generator 10 is supplied between the jaw members 113 and 114, via rods 118 and 119. This causes the coagulation of the tissue held between the jaws.

The device can also be used to simultaneously cut and coagulate tissue, using a blended waveform as previously described. As before, the jaw assembly is closed, capturing tissue between the jaw member 113 and the jaw member 114. The surgeon depresses the cut pedal 16B on the footswitch 16, and an electrosurgical waveform consisting of the start setting (100% coag) is supplied to the jaw members 113 and 114. The waveform progresses, as previously described, such that an increasing proportion of cut waveform is included, the cut waveform being supplied between the cutting rail 116 and the jaws 113 and 114. After a predetermined time period, the waveform reaches its end setting (90% cut and 10% coag), which is continued until the cut pedal 16B is released.

While the invention has been described in connection with what is presently considered to be preferred embodiments, it is to be understood that the invention is not to be limited to the disclosed embodiments, but on the contrary, is intended to cover various modifications and equivalent arrangements included within the spirit and scope of the appended claims.

What is claimed is:

1. An electrosurgical generator system for generating radio frequency power, comprising:
(i) a radio frequency output stage having three or more output connections,
(ii) one or more sources of radio frequency output power coupled to the output stage,
(iii) a controller operable to cause the system to supply a first cutting RF waveform to the output connections or a second coagulating RF waveform to the output connections, and, in a combined mode, to deliver both first and second RF waveforms, the controller including means for feeding the waveforms to the output connections such that the first RF waveform is delivered between a first pair of the output connections, and the second RF waveform is delivered between a second pair of the output connections, the arrangement of the system being such that the combined mode is adjustable between various settings, each setting having a different proportion of the first and second RF waveforms, and that, in response to an operator-actuated input signal, the controller causes the system to supply an output waveform sequence starting at a predetermined start setting, ending at a predetermined end setting, and changing between the start and end settings according to a predetermined progression.

2. A system according to claim 1, wherein the first RF cutting waveform is a waveform in which the radio frequency output voltage developed across the output connections is limited to at least a first predetermined threshold value for cutting or vaporisation of tissue, and the second RF coagulation waveform is a waveform in which the radio frequency output voltage developed across the output connections is limited to a second threshold value for coagulation.

3. A system according to claim 1, wherein the combined mode is provided by the controller operating to supply a blended output waveform sequence alternating constantly between the first RF cutting waveform and the second RF coagulating waveform.

4. A system according to claim 3, wherein the various settings each have a first predetermined duty cycle of the first RF waveform, and a second predetermined duty cycle of the second RF waveform.

5. A system according to claim 4, wherein the start setting has a second duty cycle that is between 70% and 100% of the overall delivered output.

6. A system according to claim 5, wherein the start setting has a second duty cycle that is between 90% and 100% of the overall delivered output.

7. A system according to claim 4, wherein the end setting has a first duty cycle that is between 70% and 100% of the overall delivered output.

8. A system according to claim 7, wherein the end setting has a first duty cycle that is between 90% and 100% of the overall delivered output.

9. A system according to claim 4, wherein the start setting is a waveform having a first duty cycle that is 100% of the overall delivered output, and the end setting is a blended waveform having a second duty cycle that is 90% of the overall delivered output.

10. A system according to claim 1, wherein the predetermined start setting has a waveform combination such that the proportion of the second RF waveform is greater than the proportion of the first RF waveform.

11. A system according to claim 1, wherein the predetermined end setting has a waveform combination such that the proportion of the first RF waveform is greater than the proportion of the second RF waveform.

12. A system according to claim 1, wherein the predetermined progression from the start setting to the end setting is an even progression over a predetermined time.

13. A system according to claim 1, wherein the controller is adapted to supply an overall delivered output waveform sequence in the form of a series of pulses.

14. A system according to claim 13, wherein the pulses are provided at a frequency of between 0.5 and 50 Hz.

15. A system according to claim 14, wherein the pulses are provided at a frequency of between 15 and 25 Hz.

16. An electrosurgical system including electrosurgical generator apparatus for generating radio frequency power, and an electrosurgical instrument including at least three electrodes, the generator apparatus comprising (i) a radio frequency output stage having at least three output connections in electrical communication with the electrodes of the instrument,
(ii) a power supply coupled to the output stage for supplying power to the output stage,
(iii) a controller operable to cause the generator apparatus to supply a blended output waveform sequence alternating constantly between a first output waveform across the output connections in which the radio frequency output voltage developed across the output connections is limited to at least a first predetermined threshold value for cutting or vaporisation of tissue, and a second output waveform across the output connections in which the radio frequency output voltage developed across the output connections is limited to a second threshold value for coagulation, the controller including means for feeding the waveforms to the output connections such that the first output waveform is delivered between a first pair of the output connections, and the second output waveform is delivered between a second pair of the output connections, the controller being capable of causing the generator apparatus to deliver the waveforms in various settings, the various settings each having a first predetermined duty cycle of the waveform that is limited to the first threshold value for cutting or vaporisation, and a second predetermined duty cycle of the waveform that is limited to the second threshold value for coagulation, the arrangement of the generator apparatus being such that, in response to a operator-actuated input signal, the controller causes the generator apparatus to supply an output waveform sequence starting at a predetermined start setting, ending at a predetermined end setting, and changing between the start and end settings according to a predetermined progression.

17. A system according to claim 16, wherein at least two of the electrodes are in the form of a pair of jaws.

18. An electrosurgical system comprising:
(i) a bipolar electrosurgical instrument including a handle, a jaw assembly arranged such that manipulation of the handle allows the opposed jaws of the jaw assembly to be opened and closed with respect to one another; a first of said opposed jaws having at least a first coagulating electrode; the other of said opposed jaws having at least a second coagulating electrode; and a cutting electrode, the cutting electrode being separated from the second coagulating electrode by an insulating member, and
(ii) electrosurgical generator apparatus comprising one or more sources of RF output power, a controller operable to control the generator such that it is capable of providing a first cutting RF waveform to the electrosurgical instrument or a second coagulating RF waveform to the electrosurgical instrument, and, in a combined mode, to deliver both first and second RF waveforms, the waveforms being fed to the electrosurgical instrument such that, in the combined mode, the cutting RF waveform is delivered between the cutting electrode and at least one of the first and second coagulating electrodes, and the coagulating RF waveform is delivered between the first and second coagulating electrodes, the combined mode being adjustable between various settings, each setting having a different proportion of the first and second RF waveforms, the arrangement of the generator apparatus being such that, in response to an operator-actuated input signal, the controller causes the generator apparatus to supply an output waveform sequence starting at a predetermined start setting, ending at a predetermined end setting, and changing between the start and end settings according to a predetermined progression.

19. An electrosurgical generator comprising a radio frequency source, a plurality of output terminals for connection to an electrosurgical instrument, a coupling stage coupling the source to the output terminals and a control stage configured to adjust the coupling stage according to a blended treatment sequence in which radio frequency energy is supplied to the output terminals as the combination of first and second waveforms respectively for cutting or vaporising tissue and for coagulating tissue, wherein the control stage is configured such that, upon activation of the sequence, the second waveform predominates and, after a predetermined build-up period has elapsed, the first waveform predominates, the relative proportions of the two waveforms changing progressively through intermediate proportions during the build-up period.

* * * * *